(12) United States Patent
Szpilman et al.

(10) Patent No.: US 12,281,062 B2
(45) Date of Patent: Apr. 22, 2025

(54) LIGHT INDUCED CATALYTIC C—H OXYGENATION OF ALKANES

(71) Applicant: ARIEL SCIENTIFIC INNOVATIONS LTD., Ariel (IL)

(72) Inventors: Alex Martin Szpilman, Kiryat Tivon (IL); Sourav Kumar Santra, Ariel (IL)

(73) Assignee: ARIEL SCIENTIFIC INNOVATIONS LTD., Ariel (IL)

( * ) Notice: Subject to any disclaimer, the term of this patent is extended or adjusted under 35 U.S.C. 154(b) by 233 days.

(21) Appl. No.: 17/763,718

(22) PCT Filed: Sep. 27, 2020

(86) PCT No.: PCT/IL2020/051057
§ 371 (c)(1),
(2) Date: Mar. 25, 2022

(87) PCT Pub. No.: WO2021/059287
PCT Pub. Date: Apr. 1, 2021

(65) Prior Publication Data
US 2022/0363621 A1    Nov. 17, 2022

Related U.S. Application Data

(60) Provisional application No. 62/906,197, filed on Sep. 26, 2019.

(51) Int. Cl.
C07C 45/30        (2006.01)
(52) U.S. Cl.
CPC ................... *C07C 45/30* (2013.01)
(58) Field of Classification Search
CPC ....................................................... C07C 45/30
See application file for complete search history.

(56) References Cited

U.S. PATENT DOCUMENTS 5,286,902 A    2/1994    James

FOREIGN PATENT DOCUMENTS

| JP | 2002114735 A | 4/2002 |
| JP | 2008523980 A | 7/2008 |
| JP | 2010202556 A | 9/2010 |

OTHER PUBLICATIONS

Sagadevan, A., Hwang, K. C., & Su, M.-D. (2017). Singlet oxygen-mediated selective C—H bond hydroperoxidation of ethereal hydrocarbons. Nature Communications, 8(1). doi:10.1038/s41467-017-01906-5.
Dobras, G., & Orlińska, B. (2018). Aerobic oxidation of alkylaromatic hydrocarbons to hydroperoxides catalysed by N-hydroxyimides in ionic liquids as solvents. Applied Catalysis A: General, 561, 59-67. doi:10.1016/j.apcata.2018.05.012.
Fukuda, O., Sakaguchi, S. and Ishii, Y. (2001), Preparation of Hydroperoxides by N-Hydroxyphthalimide-Catalyzed Aerobic Oxidation of Alkylbenzenes and Hydroaromatic Compounds and Its Application. Adv. Synth. Catal., 343: 809-813. https://doi.org/10.1002/1615-4169(20011231)343:8<809::AID-ADSC809>3.0.CO;2-1.
A. F. Olea and F. Wilkinson. Singlet Oxygen Production from Excited Singlet and Triplet States of Anthracene Derivatives in Acetonitrile. The Journal of Physical Chemistry 1995 99 (13), 4518-4524 DOI: 10.1021/j100013a022.
Orlińska, B., Stec, Z. & Zawadiak, J. Oxidation of 2-methoxy-6-(1-methylethyl)naphthalene with oxygen. Monatsh Chem 143, 295-301 (2012). https://doi.org/10.1007/s00706-011-0630-3.
Orlińska, B., Zawadiak, J. Aerobic oxidation of isopropylaromatic hydrocarbons to hydroperoxides catalyzed by N-hydroxyphthalimide. Reac Kinet Mech Cat 110, 15-30 (2013). https://doi.org/10.1007/s11144-013-0581-2.
Santra, S. (2020). Visible solar light mediated benzylic C—H oxygenation [Poster]. The 85th Annual Meeting of the Israel Chemical Society, Jerusalem, Israel. https://program.eventact.com/Agenda/Lecture/210957?code=1853906.
S. K. Santra and A. M. Szpilman. Visible-Spectrum Solar-Light-Mediated Benzylic C—H Oxygenation Using 9,10-Dibromoanthracene as an Initiator. The Journal of Organic Chemistry 2021 86 (1), 1164-1171 DOI: 10.1021/acs.joc.0c01720.
Chen, K., Zhang, P., Wang, Y., & Li, H. (2014). Metal-free allylic/benzylic oxidation strategies with molecular oxygen: recent advances and future prospects. Green Chemistry, 16(5), 2344. doi:10.1039/c3gc42135j.
International Search Report of PCT/IL2020/051057 Completed Nov. 29, 2020; Mailed Nov. 30, 2020 4 pages.
Written Opinion of PCT/IL2020/051057 Completed Nov. 29, 2020; Mailed Nov. 30, 2020 7 pages.
Saha, B., & Espenson, J. H. (2004). Bromoanthracenes and metal co-catalysts for the autoxidation of para-xylene. Journal of Molecular Catalysis A: Chemical, 207(2), 123-129. doi: 10.1016/s1381-1169(03)00490-4.
Sugai, T., & Itoh, A. (2007). Aerobic photo-oxidation in the presence of catalytic allylbromide. Tetrahedron Letters, 48 (16), 2931-2934. doi:10.1016/j.tetlet.2007.02.060.

*Primary Examiner* — Sikarl A Witherspoon
(74) *Attorney, Agent, or Firm* — The Roy Gross Law Firm, LLC; Roy Gross

(57) ABSTRACT

A method of oxygenating a benzylic C—H bond is provided. The method comprises light induced activation of an initiator and subsequent reaction with oxygen, resulting in the formation of free radicals. Subsequently, free radicals catalyze the reaction of the benzylic C—H bond with oxygen, thereby forming an oxygenated compound.

12 Claims, 4 Drawing Sheets

| Entry | Initiator (mol%) | R | Concentration | t(react) | Conversion | Ratio of 3/4/5[d] |
|---|---|---|---|---|---|---|
| 5[a] | 9,10-Dibromoanthracene (10) | H | 0.04 mol/L | 8 h | 100% | 78 / 9 / 13 |
| 6 | 9,10-Dibromoanthracene (10) | H | 0.04 mol/L | 9 h | 95% | 81 / 10 / 9 |
| 7 | Anthraquinone (10) | H | 0.04 mol/L | 9 h | 75% | 14 / 28 / 58 |
| 8[b] | 9,10-Dibromoanthracene (10) | H | 0.04 mol/L | 18 h | 53% | 77 / 10 / 13 |
| 9[c] | 9,10-Dibromoanthracene (10) | H | 0.04 mol/L | 9 h | NR | - |
| 10 | 9,10-Dibromoanthracene (10) | H | 0.04 mol/L | 4 h then 5h in the dark | 59% 62% | 78 / 10 / 11 77 / 11 / 11 |
| 11 | None | H | 0.04 mol/L | 9 h | NR | - |
| 12 | 9,10-Dibromoanthracene (10), TEMPO 10 mol% | H | 0.04 mol/L | 9 h | NR | - |
| 13 | 9,10-Dibromoanthracene (10), HBr (10)[e] | H | 0.04 mol/L | 9 h | 87% | 70/14/15 |
| 14 | 9,10-Dibromoanthracene (5), NHPI (5) | H | 0.04 mol/L | 10 h | 96% | 60 / 24 / 16 |
| 15 | 9,10-Dibromoanthracene (1), NHPI (15) | H | 0.04 mol/L | 10 h | 91% | 86 / 10 / 4 |
| 16[a,f] | 9,10-Dibromoanthracene (10) | H | 0.04 mol/L | 33 h | 93% | 47/21/32 |
| 17 | 9,10-Dibromoanthracene (10) | OMe | 0.04 mol/L | 4 h | 89% | 54/0/46 |
| 18 | 9,10-Dibromoanthracene (10) | OMe | 0.04 mol/L | 7 h | 100% | 0/0/100 |
| 19 | 9,10-Dibromoanthracene (10) | Cl | 0.04 mol/L | 9 h | 94% | 77/6/16 |

Figure 1 continued

LIGHT INDUCED CATALYTIC C—H OXYGENATION OF ALKANES

CROSS-REFERENCE TO RELATED APPLICATIONS

This application is a National Phase of PCT Patent Application No. PCT/IL2020/051057 having International filing date of Sep. 27, 2020, which claims the benefit of priority of U.S. Provisional Patent Application No. 62/906,197 filed Sep. 26, 2019, the contents of which are incorporated herein by reference in their entirety.

FIELD OF THE INVENTION

The invention relates inter alia to a method of oxygenating a benzylic C—H bond by a catalytic radical reaction.

BACKGROUND

Due to the ability to convert non-functionalized commodity chemicals into functionalized products, the oxidation of C—H bonds is of considerable academic interest. However, such processes have already been in use for decades in the chemical industry.

One of the most important C—H activation processes is the Hock oxygenation of cumene to give cumene peroxide. Subsequent acid catalysed thermal C—C bond breakage of cumene peroxide is one of the main processes for the production of phenol and acetone. Several million tons of phenol and acetone are produced annually through this process.

The current industrial C—H oxygenation process is a thoroughly optimised version of the seminal work by Hock. In an exemplary industrial process cumene is subjected to 1-7 atmospheres of air or pure oxygen at 80-120° C. in the presence of a sub stoichiometric amount of cumene hydroperoxide as an initiator to afford a mixture of cumene peroxide, unreacted cumene and various other side products including acetophenone, phenol and hydroxyacetone. Due to low conversion (typically 20-40%), remaining cumene is removed in a concentrator unit and resubmitted to the reaction conditions.

Commonly, 2 to 4 bubble reactors are used to achieve a high overall conversion of cumene to cumene hydroperoxide. Typical mean residence time is around 10 hours. The combination of low conversion, high temperature, and pressure and heavy infrastructure required, and the need to separate and resubmit the reaction stream multiple times makes the process highly inefficient. This is accompanied by a tedious and dangerous separation of by-products from the desired product (cumene peroxide).

Therefore, there is a need to develop new industrially applicable procedures for the oxidation of the benzylic C—H bond.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

In one aspect of the present invention, there is provided a method of modifying a benzylic C—H bond, thereby forming a compound represented by Formula 1:

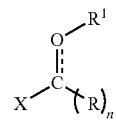

the method comprising:
reacting a substrate comprising the benzylic C—H bond with oxygen in the presence of an initiator, under conditions sufficient to form the compound, wherein:
‑ ‑ ‑ ‑ ‑ ‑   represents any one of: (i) a single bond if n is 2; and (ii) a double bond if n is 1;
X comprises an aromatic ring;
R is selected from the group consisting of: an alkyl, an aryl, hydrogen, and a cycloalkyl;
$R^1$ is selected from the group consisting of: hydrogen, hydroxy, or is absent;
the initiator generates a radical upon excitation;
and n is 1 to 2.

In one embodiment, the conditions comprise providing an energy source sufficient to excite the initiator In one embodiment, the energy source is a light source generating light in a range sufficient to excite the initiator In one embodiment, the range is from 200 to 900 nm.

In one embodiment, the radical is a halogen radical.

In one embodiment, the conditions comprise a temperature in a range from 0 to 100° C.

In one embodiment, the conditions comprise a reaction time in a range from 1 to 40 h.

In one embodiment, the reacting further comprises mixing the substrate and the initiator with a solvent, thereby forming a reaction mixture.

In one embodiment, the substrate is at a concentration ranging from 0.01 to 2 mol/L within the reaction mixture.

In one embodiment, a molar ratio of the substrate to the initiator is at least 1:0.01.

In one embodiment, the initiator is represented by Formula 4:

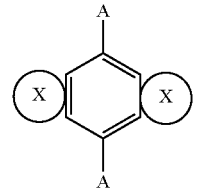

wherein:
each X independently comprises an aromatic cycloalkane or an aliphatic cycloalkane;
and each A independently represents a halo group.

In one embodiment, the aromatic cycloalkane is selected from the group consisting of: an aromatic ring, a fused aromatic ring, a substituted aromatic ring.

In one embodiment, the singlet oxygen generating compound is 9,10-dibromoanthracene.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1:
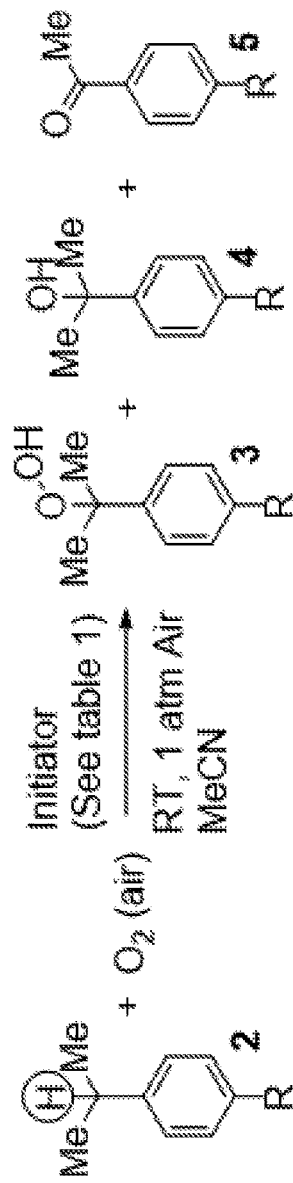
FIG. 1 presents a table (also referred to herein as Table 1) showing optimization of the reaction conditions for the light induced catalytic oxygenation of cumene [2]. The table presents several reaction conditions with respect to the conversion ratio of [2] and to the selectivity of the reaction, being represented by molar ratios of [3]:[4]:[5]. a: Blue LED (light power is 100 Watt) was used instead of sunlight. b: Glass filter w. cut-off at 360 nm in presence of LED lamp. c: Reaction carried out in darkness. d: cumene hydroperoxide is explosive. e: added as an aliquot from a 48% aqueous solution. f: carried out on 1.2 gram scale of cumene. Conversion, product ratios and yields were therefore determined by NMR analysis of the reaction mixture. NHPI is N-Hydroxyphthalimide. The reaction shown in Entry 1 is performed in a Pyrex reactor with light wavelength cut-off of 330 nm.

The present invention in one aspect thereof, is directed to a method of oxygenating a benzylic C—H bond, the method comprises reacting the benzylic C—H bond with oxygen in the presence of an initiator under suitable conditions, wherein the initiator generates a radical upon excitation.

The present invention is based in part on a surprising finding, that a sub-stoichiometric amount of photo-activated 9,10-dibromo-anthracene is sufficient to induce a selective oxygenation of a benzylic C—H bond.

Process

In one aspect of the invention, there is a method of modifying a benzylic C—H bond, thereby forming a compound represented by Formula 1:

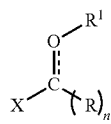

the method comprises: reacting a substrate comprising benzylic C—H bond with oxygen in the presence of an initiator, under conditions sufficient to form the compound, wherein:
n is 0 to 2;
------ represents any one of: (i) a single bond if n is 2; and (ii) a double bond if n is 0-1;
X comprises an aromatic ring;
R is selected from the group consisting of: an alkyl, an aryl, and a cycloalkyl or any combination thereof;
$R^1$ is selected from the group consisting of: hydrogen, hydroxy, or is absent;
and the initiator generates a radical upon excitation.

In some embodiments, there is a method of modifying a benzylic C—H bond, thereby forming a compound represented by Formula 1:

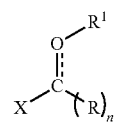

the method comprises: reacting a substrate comprising benzylic C—H bond with oxygen in the presence of an initiator, under conditions sufficient to form the compound, wherein:
n is 1 or 2;
------ represents any one of: (i) a single bond if n is 2; and (ii) a double bond if n is 1;
X comprises an aromatic ring;
i.------ represents a double bond, then R is selected from the group consisting of: hydrogen, an alkyl, an aryl, and a cycloalkyl or any combination thereof; and
i.------ represents a single bond, then R is selected from the group consisting of: an alkyl, an aryl, and a cycloalkyl or any combination thereof;
$R^1$ is selected from the group consisting of: hydrogen, hydroxy, or is absent;
and the initiator generates a radical upon excitation.

In some embodiments, there is a method for oxygenating a compound comprising a benzylic C—H bond, a sulfide bond or both, the method comprises reacting the compound with oxygen in the presence of an initiator, under conditions sufficient for oxygenating the compound, wherein the initiator generates a radical upon excitation. In some embodiments, the method comprises oxygenating a sulfide bond, thereby forming a sulfone bond. In some embodiments, the method is for oxygenating an aryl-sulfide bond, so as to form an aryl-sulfone bond.

In some embodiments, the method comprises a reaction illustrated by Scheme 1:

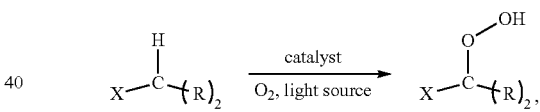

wherein X and R are as defined hereinabove.

In some embodiments, the method comprises a reaction illustrated by Scheme 2:

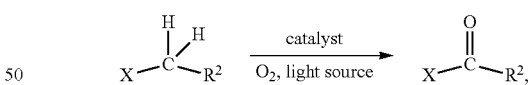

wherein $R^2$ is selected from the group consisting of: an alkyl, hydrogen, an aryl, and a cycloalkyl or any combination thereof. In some embodiments, $R^2$ optionally comprises a heteroatom, a substituent or both.

In some embodiments, the method comprises a reaction illustrated by Scheme 3a:

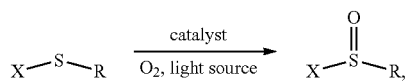

wherein X is as described hereinabove, and R comprises an alkyl, an aryl, a cycloalkyl and hydrogen or a combination thereof.

In some embodiments, the method comprises a reaction illustrated by Scheme 3b:

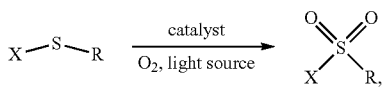

wherein X and R are as defined hereinabove.

In some embodiments, a substrate is a compound comprising a benzylic C—H bond. In some embodiments, the substrate comprises one or more benzylic C—H bonds. In some embodiments, the substrate comprises a plurality of benzylic C—H bonds.

As used herein, the term "benzylic" is related to a carbon atom in alpha-position (i.e., directly bound) to an aromatic ring.

In some embodiments, the substrate comprises one or more aromatic rings. In some embodiments, the substrate comprises one or more fused aromatic rings. In some embodiments, the substrate comprises one or more fused aromatic rings. In some embodiments, the substrate comprises one or more hetero-aromatic rings.

In some embodiments, the substrate (e.g. the aromatic ring) further comprises one or more reactive groups.

Non-limiting examples of a reactive group include but are not limited to: an ester group, a hydroxy group, a halo group, an amide group, an alkoxy group, a carbonyl group, an aryloxy group, a thioaryloxy group, a mercapto group, a cyano group, a thioalkoxy group, an amino group, an azo group, a vinyl group, a phosphinyl group, or a combination thereof.

In some embodiments, the substrate comprises a compound represented by Formula 1, wherein X is an aromatic or a heteroaromatic ring, and wherein X optionally comprises a substituent.

In some embodiments, X comprises a heteroaromatic ring. In some embodiments, X comprises a bicyclic aromatic ring, optionally comprising a heteroatom. In some embodiments, X comprises a fused aromatic ring, optionally comprising a heteroatom. In some embodiments, X comprises a bridged aromatic ring, optionally comprising a heteroatom.

In some embodiments, the substrate comprises a compound represented by Formula 1A1:

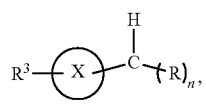

wherein each R is as described herein; X represents an aromatic ring or a heteroaromatic ring, substituted or not substituted; and n is 1 or 2.

In some embodiments, $R^3$ represents a hydrogen or at least one substituent. In some embodiments, $R^3$ represents a substituent independently comprising halogen, $NO_2$, CN, optionally substituted $C_1$-$C_6$ alkyl, $C_1$-$C_6$ haloalkyl, $NH_2$, $NH(C_1$-$C_6$ alkyl), $N(C_1$-$C_6$ alkyl)$_2$, OH, $C_1$-$C_6$ alkoxy, $C_1$-$C_6$ haloalkoxy, hydroxy($C_1$-$C_6$ hydroxy($C_1$-$C_6$ alkoxy), alkoxy($C_1$-$C_6$ alkyl), alkoxy($C_1$-$C_6$ alkoxy), amino($C_1$-$C_6$ alkyl), $CONH_2$, $CONH(C_1$-$C_6$ alkyl), $CON(C_1$-$C_6$ alkyl)$_2$, $CO_2H$, $CO_2(C_1$-$C_6$ alkyl), $CO_2(C_3$-$C_8$ heterocyclyl), $CO_2$ ($C_3$-$C_8$ cycloalkyl), $CO_2(C_5$-$C_8$ heteroaryl), $CO_2(C_5$-$C_8$ aryl), $CO_2(C_6$-$C_{20}$ polycyclic aryl), $CO_2(C_6$-$C_{20}$ polycyclic heteroaryl), $CO_2(C_6$-$C_{20}$ bicyclic aryl), $CO_2(C_6$-$C_{20}$ bicyclic heteroaryl), $C_1$-$C_6$ alkaryl, $SO_2R$, $SO_2OR$, $SO_2N(R)_2$, cyclopropylethynyl, optionally substituted $(C_5$-$C_{20})$aryl, optionally substituted $(C_5$-$C_{20})$heteroaryl, optionally substituted heterocyclyl, and optionally substituted $C_3$-$C_8$ cycloalkyl or a combination thereof. In some embodiments, $R^3$ is devoid of para-hydroxy($C_1$-$C_6$ alkyl).

In some embodiments, X comprises an optionally substituted heteroaryl, optionally substituted aryl, optionally substituted polycyclic heteroaryl, optionally substituted polycyclic aryl, optionally substituted bicyclic heteroaryl, optionally substituted bicyclic aryl, optionally substituted bicyclic heterocyclyl, or a combination thereof. In some embodiments, X comprises an optionally substituted aromatic $(C_5$-$C_{10})$ ring or a combination thereof. In some embodiments, X comprises an aromatic ($C_5$ or a $C_6$) ring, a bicyclic aliphatic $(C_5$-$C_{20})$ ring, a bicyclic aromatic $(C_6$-$C_{20})$ ring, or a combination thereof, wherein each ring is optionally substituted.

As used herein the term "$C_1$-$C_6$ alkyl" including any $C_1$-$C_6$ alkyl related compounds, is referred to any linear or branched alkyl chain comprising between 1 and 6, between 1 and 2, between 2 and 3, between 3 and 4, between 4 and 5, between 5 and 6, carbon atoms, including any range therebetween. In some embodiments, $C_1$-$C_6$ alkyl comprises any of methyl, ethyl, propyl, butyl, pentyl, iso-pentyl, hexyl, and tert-butyl or any combination thereof. In some embodiments, $C_1$-$C_6$ alkyl as described herein further comprises an unsaturated bond, wherein the unsaturated bond is located at $1^{st}$, $2^{nd}$, $3^{rd}$, $4^{th}$, $5^{th}$ or $6^{th}$ position of the $C_1$-$C_6$ alkyl.

As used herein the term "$(C_5$-$C_{10})$ ring" is referred to an optionally substituted C5, C6, C7, C8, C9 or C10 ring.

As used herein the term "$(C_3$-$C_8)$ cycloalkyl" is referred to an optionally substituted C5, C6, C7, or C8 cycloalkyl. In some embodiments, $(C_5$-$C_8)$ cycloalkyl comprises optionally substituted cyclopropane, cyclobutene, cyclopentane, cyclohexane, or cycloheptane.

As used herein the term "$(C_5$-$C_{20})$ aryl" is referred to an optionally substituted C5, C6, C7, C8, C9, C10, C11, C12, C13, C14, C15, C16, C17, C18, C19, C20, aromatic ring including any range therebetween. In some embodiments, $(C_5$-$C_{20})$ aryl comprises a 5 to 20, 5 to 6, 6 to 8, 8 to 10, 10 to 12, 12 to 15, 15 to 20 membered optionally substituted aromatic ring, including any value therebetween.

As used herein the term "$(C_5$-$C_{20})$ heteroaryl" is referred to an optionally substituted C5, C6, C7, C8, C9, C10, C11, C12, C13, C14, C15, C16, C17, C18, C19, C20, heteroaromatic ring including any range therebetween. In some embodiments, $(C_5$-$C_{20})$ heteroaryl comprises a 5 to 20, 5 to 6, 6 to 8, 8 to 10, 10 to 12, 12 to 15, 15 to 20 membered optionally substituted heteroaromatic ring, including any value therebetween.

Non-limiting examples of heteroaryls include but are not limited to: pyrrole, furan, thiophene, thiazole, pyrazole, isothiazole, imidazole or any combination thereof, optionally substituted with one or more $R_3$.

Non-limiting examples of bicyclic heteroaryls include but are not limited to: indole, isoindole, benzothiazole, benzoxazole, benzofuran, isobenzofuran, benzothiophene, benzotriazole, quinoline, chromene, chroman, quinazoline, 1-benzothiophene, 2-benzothiophene, indazole, and purine or any combination thereof, optionally substituted with one or more $R_3$.

Non-limiting examples of polycyclic aryls include but are not limited to: naphthalene, biphenyl, fluorene, anthracene, phenanthrene, phenalene, tetracene, chrysene, triphenylene, pyrene, pentacene, perylene, benzopyrene, corannulene, ovalene, and benzofluorene or any combination thereof.

Other non-limiting examples of polycyclic heteroaryls include but are not limited to: azepine, acridine, benzimidazole, benzindole, 1,3-benzodioxole, benzofuran, benzoxazole, benzothiazole, benzothiadiazole, benzo[b][1,4]dioxepine, benzo[b][1,4]oxazine, 1,4-benzodioxane, bipyridine, benzonaphthofuran, benzoxazole, benzodioxol, benzodioxine, benzopyran, benzopyranon, benzofuran, benzofuranon, benzothiene (benzothiophene), benzothieno[3,2-d]pyrimidine, benzotriazole, benzo[4,6]imidazo[1,2-a]pyridine, carbazole, cinnoline, cyclopenta[d]pyrimidine, 6,7-dihydro-5H-cyclopenta[4,5]thieno[2,3-d]pyrimidine, 5,6-dihydrobenzo[h]quinazoline, 5,6-dihydrobenzo[h]cinnoline, 7',8'-dihydro-5'H-spiro[[1,3]dioxolane-2,6'-quinoline]-3'-e, 6,7-dihydro-5H-benzo[6,7]cyclohepta[1,2-c]pyridazine, dibenzofurane, dibenzothiophene, furane, furanone, furo[3,2-c]pyridine, furopyrimidine, furopyridazine, furopyrazine, isothiazole, imidazole, imidazopyrimidine, imidazopyridazine, imidazopyrazine, indazole, indole, indazole, isoindole, indoline, isoindoline, isoquinoline, indolizine, isoxazole, naphthyridine, 1,6-naphthyridinone, oxadiazole, 2-oxoazepine, oxazole, oxirane, 5,6,6a,7,8,9,10,10a-octahydrobenzo[h]quinazoline, 1-phene-1H-pyrrole, phenazine, phenothiazine, phenoxazine, phthalazine, phenanthridine, pteridine, purine, pyrrole, pyrazole, pyrazolo[3,4-d]pyrimidine, pyridine, pyrido[3,2-d]pyrimidine, pyrido[3,4-d]pyrimidine, pyrazine, pyrimidine, pyridazine, bipyridazine, pyrrole, pyrrolopyrimidine, pyrrolopyridazine, pyrrolopyrazine, quinazoline, quinoxaline, quinoline, quinuclidine, isoquinoline, tetrahydroquinoline, 5,6,7,8-tetrahydroquinazoline, 2,3,4,5-tetrahydrobenzo[b]oxepine, 3,4-dihydro-2H-benzo[b][1,4]dioxepine, 6,7,8,9-tetrahydro-5H-cyclohepta[b]pyridine, 6,7,8,9-tetrahydro-5H-pyrido[3,2-c]azepine, 5,6,7,8-tetrahydrobenzo[4,5]thieno[2,3-d]pyrimidine, 6,7,8,9-tetrahydro-5H-cyclohepta[4,5]thieno[2,3-d]pyrimidine, 5,6,7,8-tetrahydropyrido[4,5-c]pyridazine, thiazole, thiadiazole, triazole, tetrazole, 1,2,3,4-tetrahydroisoquinolin-7-e, triazine, thieno[2,3-d]pyrimidine, thienopyrimidine (e.g., thieno[3,2-d]pyrimidine), thieno[2,3-c]pyridine, thienopyridazine, thienopyrazine or any combination thereof.

In some embodiments, a substituted aromatic or aliphatic ring, comprises one or more substituent as described herein. In some embodiments, a substituted aromatic or aliphatic ring, comprises one or more substituent, wherein the substituent is represented by $R^3$.

In some embodiments, at least one R and X are connected together so as to form a bicyclic ring. In some embodiments, at least one R and X are connected together so as to form a fused ring.

In some embodiments, R comprises halogen, hydrogen, $NO_2$, CN, optionally substituted $C_1$-$C_6$ alkyl, $(C_1$-$C_6)$alkyl-COOH, $C_1$-$C_6$ haloalkyl, $NH_2$, $NH(C_1$-$C_6$ alkyl), $N(C_1$-$C_6$ alkyl)$_2$, $N^+(C_1$-$C_6$ alkyl)$_3$, $NH(C_1$-$C_6$ alkaryl), $N(C_1$-$C_6$ alkaryl)$_2$, $N^+(C_1$-$C_6$ alkaryl)$_3$, $NH(C_5$-$C_{20}$ aryl), $N(C_5$-$C_{20}$ aryl)$_2$, $(C_1$-$C_6)$alkyl-$N(C_1$-$C_6$ alkyl)$_2$, $(C_1$-$C_6)$alkyl-$NH(C_1$-$C_6$ alkyl), $(C_1$-$C_6)$alkyl-$O(C_1$-$C_6$ alkyl), $(C_1$-$C_6)$alkyl-$S(C_1$-$C_6$ alkyl), OH, $C_1$-$C_6$ alkoxy, $C_1$-$C_6$ haloalkoxy, hydroxy$(C_1$-$C_6$ alkyl), hydroxy$(C_1$-$C_6$ alkaryl), hydroxy$(C_5$-$C_{20}$aryl), SH, $S(C_1$-$C_6$ alkyl), $S(C_1$-$C_6$ alkaryl), $SOO(C_5$-$C_{20}$aryl), $SOO(C_1$-$C_6$ alkyl), $SOO(C_1$-$C_6$ alkaryl), $SOO(C_5$-$C_{20}$aryl), hydroxy$(C_1$-$C_6$ alkoxy), alkoxy$(C_1$-$C_6$ alkyl), alkoxy$(C_1$-$C_6$ alkoxy), amino$(C_1$-$C_6$ alkyl), $C_1$-$C_6$ alkaryl, $CONH_2$, $CONH(C_1$-$C_6$ alkyl), $CON(C_1$-$C_6$ alkyl)$_2$, $(C_5$-$C_{20})$aryl, $(C_5$-$C_{20})$heteroaryl, $CO_2H$, $C_1$-$C_6$ alkyl-$CO_2H$, $(C_1$-$C_6)$alkyl-$CO_2(C_1$-$C_6$ alkyl), $CO_2(C_1$-$C_6$ alkyl), $CO_2(C_1$-$C_6$ alkaryl), $CO_2(C_1$-$C_6$ alkylheteroaryl), $(C_1$-$C_6)$alkyl-$CO_2(C_1$-$C_6$ alkaryl), $(C_1$-$C_6)$alkyl-$CO_2(C_1$-$C_6$ alkylheteroaryl), or any combination thereof.

In some embodiments, the substrate comprises a compound represented by Formula 1B1:

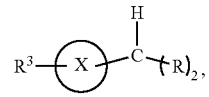

wherein $R^3$ is as described herein, and wherein each R independently comprises halogen, $NO_2$, CN, optionally substituted $C_1$-$C_6$ alkyl, $(C_1$-$C_6)$alkyl-COOH, $C_1$-$C_6$ haloalkyl, $NH_2$, $NH(C_1$-$C_6$ alkyl), $N(C_1$-$C_6$ alkyl)$_2$, $N^+(C_1$-$C_6$ alkyl)$_3$, $NH(C_1$-$C_6$ alkaryl), $N(C_1$-$C_6$ alkaryl)$_2$, $N^+(C_1$-$C_6$ alkaryl)$_3$, $NH(C_5$-$C_{20}$ aryl), $N(C_5$-$C_{20}$ aryl)$_2$, $(C_1$-$C_6)$alkyl-$N(C_1$-$C_6$ alkyl)$_2$, $(C_1$-$C_6)$alkyl-$NH(C_1$-$C_6$ alkyl), $(C_1$-$C_6)$alkyl-$O(C_1$-$C_6$ alkyl), $(C_1$-$C_6)$alkyl-$S(C_1$-$C_6$ alkyl), OH, $C_1$-$C_6$ alkoxy, $C_1$-$C_6$ haloalkoxy, hydroxy$(C_1$-$C_6$ alkyl), hydroxy$(C_1$-$C_6$ alkaryl), hydroxy$(C_5$-$C_{20}$aryl), SH, $S(C_1$-$C_6$ alkyl), $S(C_1$-$C_6$ alkaryl), $SOO(C_5$-$C_{20}$aryl), $SOO(C_1$-$C_6$ alkyl), $SOO(C_1$-$C_6$ alkaryl), $SOO(C_5$-$C_{20}$aryl), hydroxy$(C_1$-$C_6$ alkoxy), alkoxy$(C_1$-$C_6$ alkyl), alkoxy$(C_1$-$C_6$ alkoxy), amino$(C_1$-$C_6$ alkyl), $C_1$-$C_6$ alkaryl, $CONH_2$, $CONH(C_1$-$C_6$ alkyl), $CON(C_1$-$C_6$ alkyl)$_2$, $(C_5$-$C_{20})$aryl, $(C_5$-$C_{20})$heteroaryl, $CO_2H$, $C_1$-$C_6$ alkyl-$CO_2H$, $(C_1$-$C_6)$alkyl-$CO_2(C_1$-$C_6$ alkyl), $CO_2(C_1$-$C_6$ alkyl), $CO_2(C_1$-$C_6$ alkaryl), $CO_2(C_1$-$C_6$ alkylheteroaryl), $(C_1$-$C_6)$alkyl-$CO_2(C_1$-$C_6$ alkaryl), $(C_1$-$C_6)$alkyl-$CO_2(C_1$-$C_6$ alkylheteroaryl), or any combination thereof. In some embodiments, at least one R and X are connected together so as to form a bicyclic ring. In some embodiments, at least one R and X are connected together so as to form a fused ring.

In some embodiments, the substrate comprises a compound represented by Formula 1B2:

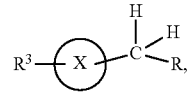

wherein $R^3$ is as described herein, and wherein R comprises hydrogen, halogen, $NO_2$, CN, optionally substituted $C_1$-$C_6$ alkyl, $(C_1$-$C_6)$alkyl-COOH, $C_1$-$C_6$ haloalkyl, $NH_2$, $NH(C_1$-$C_6$ alkyl), $N(C_1$-$C_6$ alkyl)$_2$, $N^+(C_1$-$C_6$ alkyl)$_3$, $NH(C_1$-$C_6$ alkaryl), $N(C_1$-$C_6$ alkaryl)$_2$, $N^+(C_1$-$C_6$ alkaryl)$_3$, $NH(C_5$-$C_{20}$ aryl), $N(C_5$-$C_{20}$ aryl)$_2$, $(C_1$-$C_6)$alkyl-$N(C_1$-$C_6$ alkyl)$_2$, $(C_1$-$C_6)$alkyl-$NH(C_1$-$C_6$ alkyl), $(C_1$-$C_6)$alkyl-$O(C_1$-$C_6$ alkyl), $(C_1$-$C_6)$alkyl-$S(C_1$-$C_6$ alkyl), OH, $C_1$-$C_6$ alkoxy, $C_1$-$C_6$ haloalkoxy, hydroxy$(C_1$-$C_6$ alkyl), hydroxy$(C_1$-$C_6$ alkaryl), hydroxy$(C_5$-$C_{20}$aryl), SH, $S(C_1$-$C_6$ alkyl), $S(C_1$-$C_6$ alkaryl), $SOO(C_5$-$C_{20}$aryl), $SOO(C_1$-$C_6$ alkyl), $SOO(C_1$-$C_6$ alkaryl), $SOO(C_5$-$C_{20}$aryl), hydroxy$(C_1$-$C_6$ alkoxy), alkoxy$(C_1$-$C_6$ alkyl), alkoxy$(C_1$-$C_6$ alkoxy), amino$(C_1$-$C_6$ alkyl), $C_1$-$C_6$ alkaryl, $CONH_2$, $CONH(C_1$-$C_6$ alkyl), $CON(C_1$-$C_6$ alkyl)$_2$, $(C_5$-$C_{20})$aryl, $(C_5$-$C_{20})$heteroaryl, $CO_2H$, $C_1$-$C_6$ alkyl-$CO_2H$, $(C_1$-$C_6)$alkyl-$CO_2(C_1$-$C_6$ alkyl), $CO_2(C_1$-$C_6$ alkyl), $CO_2(C_1$-$C_6$ alkaryl), $CO_2(C_1$-$C_6$ alkylheteroaryl), $(C_1$-$C_6)$alkyl-$CO_2(C_1$-$C_6$ alkaryl), $(C_1$-$C_6)$alkyl-$CO_2(C_1$-$C_6$ alkylheteroaryl), or any combination thereof. In some embodiments, at least one R and X are connected together so as to form a bicyclic ring. In some embodiments, at least one R and X are connected together so as to form a fused ring.

In some embodiments, the substrate comprises a compound represented by Formula 1B3:

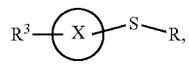

wherein R³ is as described herein, and wherein R comprises hydrogen, halogen, NO$_2$, CN, optionally substituted C$_1$-C$_6$ alkyl, (C$_1$-C$_6$)alkyl-COOH, C$_1$-C$_6$ haloalkyl, NH$_2$, NH(C$_1$-C$_6$ alkyl), N(C$_1$-C$_6$ alkyl)$_2$, N$^+$(C$_1$-C$_6$ alkyl)$_3$, NH(C$_1$-C$_6$ alkaryl), N(C$_1$-C$_6$ alkaryl)$_2$, N$^+$(C$_1$-C$_6$ alkaryl)$_3$, NH(C$_5$-C$_{20}$ aryl), N(C$_5$-C$_{20}$ aryl)$_2$, (C$_1$-C$_6$)alkyl-N(C$_1$-C$_6$ alkyl)$_2$, (C$_1$-C$_6$)alkyl-NH(C$_1$-C$_6$ alkyl), (C$_1$-C$_6$)alkyl-O(C$_1$-C$_6$ alkyl), (C$_1$-C$_6$)alkyl-S(C$_1$-C$_6$ alkyl), OH, C$_1$-C$_6$ alkoxy, C$_1$-C$_6$ haloalkoxy, hydroxy(C$_1$-C$_6$ alkyl), hydroxy(C$_1$-C$_6$ alkaryl), hydroxy(C$_5$-C$_{20}$aryl), SH, S(C$_1$-C$_6$ alkyl), S(C$_1$-C$_6$ alkaryl), SOO(C$_5$-C$_{20}$aryl), SOO(C$_1$-C$_6$ alkyl), SOO(C$_1$-C$_6$ alkaryl), SOO(C$_5$-C$_{20}$aryl), hydroxy(C$_1$-C$_6$ alkoxy), alkoxy(C$_1$-C$_6$ alkyl), alkoxy(C$_1$-C$_6$ alkoxy), amino(C$_1$-C$_6$ alkyl), C$_1$-C$_6$ alkaryl, CONH$_2$, CONH(C$_1$-C$_6$ alkyl), CON(C$_1$-C$_6$ alkyl)$_2$, (C$_5$-C$_{20}$)aryl, (C$_5$-C$_{20}$)heteroaryl, CO$_2$H, C$_1$-C$_6$ alkyl-CO$_2$H, (C$_1$-C$_6$)alkyl-CO$_2$(C$_1$-C$_6$ alkyl), CO$_2$(C$_1$-C$_6$ alkyl), CO$_2$(C$_1$-C$_6$ alkaryl), CO$_2$(C$_1$-C$_6$ alkylheteroaryl), (C$_1$-C$_6$) alkyl-CO$_2$(C$_1$-C$_6$ alkyl), (C$_1$-C$_6$)alkyl-CO$_2$(C$_1$-C$_6$ alkyl-heteroaryl), or any combination thereof. In some embodiments, at least one R and X are connected together so as to form a bicyclic ring. In some embodiments, at least one R and X are connected together so as to form a fused ring.

In some embodiments, the compound is represented by Formula 1B3 and R comprises optionally substituted C$_1$-C$_6$ alkyl, (C$_1$-C$_6$)alkyl-COOH, C$_1$-C$_6$ haloalkyl, NH$_2$, NH(C$_1$-C$_6$ alkyl), N(C$_1$-C$_6$ alkyl)$_2$, N$^+$(C$_1$-C$_6$ alkyl)$_3$, NH(C$_1$-C$_6$ alkaryl), N(C$_1$-C$_6$ alkaryl)$_2$, N$^+$(C$_1$-C$_6$ alkaryl)$_3$, NH(C$_5$-C$_{20}$ aryl), N(C$_5$-C$_{20}$ aryl)$_2$, (C$_1$-C$_6$)alkyl-N(C$_1$-C$_6$ alkyl)$_2$, (C$_1$-C$_6$)alkyl-NH(C$_1$-C$_6$ alkyl), (C$_1$-C$_6$)alkyl-O(C$_1$-C$_6$ alkyl), (C$_1$-C$_6$)alkyl-S(C$_1$-C$_6$ alkyl), C$_1$-C$_6$ alkoxy, C$_1$-C$_6$ haloalkoxy, hydroxy(C$_1$-C$_6$ alkyl), hydroxy(C$_1$-C$_6$ alkaryl), hydroxy(C$_5$-C$_{20}$aryl), alkoxy(C$_1$-C$_6$ alkoxy), amino(C$_1$-C$_6$ alkyl), C$_1$-C$_6$ alkaryl, CONH$_2$, CONH(C$_1$-C$_6$ alkyl), CON(C$_1$-C$_6$ alkyl)$_2$, (C$_5$-C$_{20}$)aryl, (C$_5$-C$_{20}$)heteroaryl, CO$_2$H, C$_1$-C$_6$ alkyl-CO$_2$H, (C$_1$-C$_6$)alkyl-CO$_2$(C$_1$-C$_6$ alkyl), CO$_2$(C$_1$-C$_6$ alkyl), CO$_2$(C$_1$-C$_6$ alkaryl), CO$_2$(C$_1$-C$_6$ alkylheteroaryl), (C$_1$-C$_6$)alkyl-CO$_2$(C$_1$-C$_6$ alkaryl), (C$_1$-C$_6$)alkyl-CO$_2$(C$_1$-C$_6$ alkylheteroaryl), or any combination thereof.

In some embodiments, the compound is represented by Formula 1B3 and R comprises optionally substituted C$_1$-C$_6$ alkyl, (C$_1$-C$_6$)alkyl-COOH, C$_1$-C$_6$ haloalkyl, NH$_2$, NH(C$_1$-C$_6$ alkyl), N(C$_1$-C$_6$ alkyl)$_2$, N$^+$(C$_1$-C$_6$ alkyl)$_3$, NH(C$_1$-C$_6$ alkaryl), N(C$_1$-C$_6$ alkaryl)$_2$, N$^+$(C$_1$-C$_6$ alkaryl)$_3$, NH(C$_5$-C$_{20}$ aryl), N(C$_5$-C$_{20}$ aryl)$_2$, (C$_1$-C$_6$)alkyl-N(C$_1$-C$_6$ alkyl)$_2$, (C$_1$-C$_6$)alkyl-NH(C$_1$-C$_6$ alkyl), (C$_1$-C$_6$)alkyl-O(C$_1$-C$_6$ alkyl), (C$_1$-C$_6$)alkyl-S(C$_1$-C$_6$ alkyl), C$_1$-C$_6$ alkoxy, C$_1$-C$_6$ haloalkoxy, alkoxy(C$_1$-C$_6$ alkoxy), amino(C$_1$-C$_6$ alkyl), C$_1$-C$_6$ alkaryl, (C$_5$-C$_{20}$)aryl, (C$_5$-C$_{20}$)heteroaryl, C$_1$-C$_6$ alkyl-CO$_2$H, (C$_1$-C$_6$)alkyl-CO$_2$(C$_1$-C$_6$ alkyl), (C$_1$-C$_6$)alkyl-CO$_2$(C$_1$-C$_6$ alkaryl), (C$_1$-C$_6$)alkyl-CO$_2$(C$_1$-C$_6$ alkylheteroaryl), or any combination thereof.

In some embodiments, the benzylic carbon is any of: a primary, a secondary, and a tertiary carbon. In some embodiments, the benzylic carbon is a part of a cyclic alkyl.

In some embodiments, the substrate is an oligomer, comprising a benzylic carbon. In some embodiments, the substrate is an oligomer comprising a plurality of benzylic carbons. In some embodiments, the substrate is a polymer comprising a plurality of benzylic carbons.

Non-limiting examples of a polymer comprising a plurality of benzylic carbons include but are not limited to: polystyrene, polydivinyl-benzene, poly(1,4-phenylene-ethylene), and poly(1,3-phenylenemethylene) or any copolymer thereof.

In some embodiments, a compound formed by the method comprises an oxygenated benzylic C—H bond.

In some embodiments, the oxygenated benzylic C—H bond comprises a hydroperoxide. In some embodiments, the present invention provides a method of forming a hydroperoxide by oxygenation of a compound of Formula 1B1. In some embodiments, the compound formed by the method of the invention is a hydroperoxide-based compound. In some embodiments, the present invention provides a method of forming a hydroperoxide by oxygenation of a tertiary benzylic carbon (e.g. when R is a substituent being devoid of hydrogen). In some embodiments, the compound formed by the method of the invention is represented by Formula 1a:

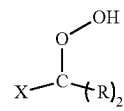

wherein X comprises an aromatic ring.

In some embodiments, R is selected from the group consisting of: an alkyl, an aryl, and a cycloalkyl. In some embodiments, R optionally comprises a heteroatom, a substituent or both.

In some embodiments, at least one R and X are connected together so as to form a bicyclic ring. In some embodiments, at least one R and X are connected together so as to form a fused ring.

In some embodiments, at least one R and X are as described hereinabove.

In some embodiments, the compound formed by the method of the invention is represented by Formula 1b:

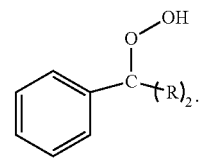

In some embodiments, the compound formed by the method of the invention is cumene hydroperoxide.

In some embodiments, the compound formed by the method of the invention is represented by Formula 1c:

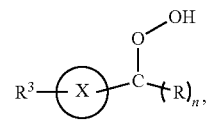

wherein X, R³ and R are as described herein, and n is 1 or 2. In some embodiments, the compound formed by the method of the invention is represented by Formula 1c, wherein R is devoid of hydrogen. In some embodiments, n is 2.

In some embodiments, the compound formed by the method of the invention is represented by Formula 1c, wherein R comprises halogen, hydrogen, NO$_2$, CN, optionally substituted C$_1$-C$_6$ alkyl, (C$_1$-C$_6$)alkyl-COOH, C$_1$-C$_6$ haloalkyl, NH$_2$, NH(C$_1$-C$_6$ alkyl), N(C$_1$-C$_6$ alkyl)$_2$, N$^+$(C$_1$-C$_6$ alkyl)$_3$, NH(C$_1$-C$_6$ alkaryl), N(C$_1$-C$_6$ alkaryl)$_2$, N$^+$(C$_1$-C$_6$ alkaryl)$_3$, NH(C$_5$-C$_{20}$ aryl), N(C$_5$-C$_{20}$aryl)$_2$, (C$_1$-C$_6$)alkyl-N(C$_1$-C$_6$ alkyl)$_2$, (C$_1$-C$_6$)alkyl-NH(C$_1$-C$_6$ alkyl), (C$_1$-C$_6$)alkyl-O(C$_1$-C$_6$ alkyl), (C$_1$-C$_6$)alkyl-S(C$_1$-C$_6$ alkyl), OH, C$_1$-C$_6$ alkoxy, C$_1$-C$_6$ haloalkoxy, hydroxy(C$_1$-C$_6$ alkyl), hydroxy(C$_1$-C$_6$ alkaryl), hydroxy(C$_5$-C$_{20}$aryl), SH, S(C$_1$-C$_6$ alkyl), S(C$_1$-C$_6$ alkaryl), SOO(C$_5$-C$_{20}$aryl), SOO(C$_1$-C$_6$ alkyl), SOO(C$_1$-C$_6$ alkaryl), SOO(C$_5$-C$_{20}$aryl), hydroxy(C$_1$-C$_6$ alkoxy), alkoxy(C$_1$-C$_6$ alkyl), alkoxy(C$_1$-C$_6$ alkoxy), amino(C$_1$-C$_6$ alkyl), C$_1$-C$_6$ alkaryl, CONH$_2$, CONH(C$_1$-C$_6$ alkyl), CON(C$_1$-C$_6$ alkyl)$_2$, (C$_5$-C$_{20}$)aryl, (C$_5$-C$_{20}$)heteroaryl, CO$_2$H, C$_1$-C$_6$ alkyl-CO$_2$H, (C$_1$-C$_6$)alkyl-CO$_2$(C$_1$-C$_6$ alkyl), CO$_2$(C$_1$-C$_6$ alkyl), CO$_2$(C$_1$-C$_6$ alkaryl), CO$_2$(C$_1$-C$_6$ alkylheteroaryl), (C$_1$-C$_6$)alkyl-CO$_2$(C$_1$-C$_6$ alkaryl), (C$_1$-C$_6$)alkyl-CO$_2$(C$_1$-C$_6$ alkylheteroaryl), or any combination thereof. In some embodiments, R is devoid of a protonated amine (e.g. a primary amine and/or a secondary amine).

In some embodiments, the compound formed by the method of the invention is represented by Formula 1d:

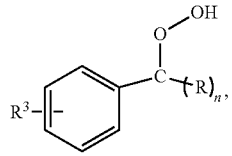

wherein R$^3$ and R are as described herein, and n is 1 or 2. In some embodiments, the compound formed by the method of the invention is represented by Formula 1d, wherein R comprises halogen, NO$_2$, CN, optionally substituted C$_1$-C$_6$ alkyl, (C$_1$-C$_6$)alkyl-COOH, C$_1$-C$_6$ haloalkyl, NH$_2$, NH(C$_1$-C$_6$ alkyl), N(C$_1$-C$_6$ alkyl)$_2$, N$^+$(C$_1$-C$_6$ alkyl)$_3$, NH(C$_1$-C$_6$ alkaryl), N(C$_1$-C$_6$ alkaryl)$_2$, N$^+$(C$_1$-C$_6$ alkaryl)$_3$, NH(C$_5$-C$_{20}$ aryl), N(C$_5$-C$_{20}$ aryl)$_2$, (C$_1$-C$_6$)alkyl-N(C$_1$-C$_6$ alkyl)$_2$, (C$_1$-C$_6$)alkyl-NH(C$_1$-C$_6$ alkyl), (C$_1$-C$_6$)alkyl-O(C$_1$-C$_6$ alkyl), (C$_1$-C$_6$)alkyl-S(C$_1$-C$_6$ alkyl), OH, C$_1$-C$_6$ alkoxy, C$_1$-C$_6$ haloalkoxy, hydroxy(C$_1$-C$_6$ alkyl), hydroxy(C$_1$-C$_6$ alkaryl), hydroxy(C$_5$-C$_{20}$aryl), SH, S(C$_1$-C$_6$ alkyl), S(C$_1$-C$_6$ alkaryl), SOO(C$_5$-C$_{20}$aryl), SOO(C$_1$-C$_6$ alkyl), SOO(C$_1$-C$_6$ alkaryl), SOO(C$_5$-C$_{20}$aryl), hydroxy(C$_1$-C$_6$ alkoxy), alkoxy(C$_1$-C$_6$ alkyl), alkoxy(C$_1$-C$_6$ alkoxy), amino(C$_1$-C$_6$ alkyl), C$_1$-C$_6$ alkaryl, CONH$_2$, CONH(C$_1$-C$_6$ alkyl), CON(C$_1$-C$_6$ alkyl)$_2$, (C$_5$-C$_{20}$)aryl, (C$_5$-C$_{20}$)heteroaryl, CO$_2$H, C$_1$-C$_6$ alkyl-CO$_2$H, (C$_1$-C$_6$)alkyl-CO$_2$(C$_1$-C$_6$ alkyl), CO$_2$(C$_1$-C$_6$ alkyl), CO$_2$(C$_1$-C$_6$ alkaryl), CO$_2$(C$_1$-C$_6$ alkylheteroaryl), (C$_1$-C$_6$)alkyl-CO$_2$(C$_1$-C$_6$ alkaryl), (C$_1$-C$_6$)alkyl-CO$_2$(C$_1$-C$_6$ alkylheteroaryl), or any combination thereof; and wherein n is 2.

In some embodiments, the oxygenated C—H bond is a carbonyl (e.g. aldehyde or ketone). In some embodiments, the present invention provides a method of forming a carbonyl by oxygenating a compound of Formula 1B2, wherein oxygenating is as described hereinabove. In some embodiments, the present invention provides a method of forming a carbonyl by oxygenation of a primary and/or a secondary benzylic carbon. In some embodiments, the compound (e.g. a carbonyl-based compound) formed by the method of the invention is represented by Formula 2:

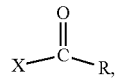

wherein R and X are as described hereinabove.

In some embodiments, R and X are connected together so as to form a fused ring represented by Formula 2a:

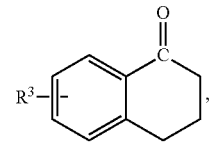

wherein R$^3$ is as described herein.

In some embodiments, the compound formed by the method of the invention is represented by Formula 2a1:

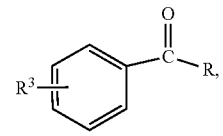

wherein R and W are as described herein.

In some embodiments, the compound formed by the method of the invention is represented by Formula 2a1, wherein R comprises hydrogen halogen, NO$_2$, CN, optionally substituted C$_1$-C$_6$ alkyl, (C$_1$-C$_6$)alkyl-COOH, C$_1$-C$_6$ haloalkyl, NH$_2$, NH(C$_1$-C$_6$ alkyl), N(C$_1$-C$_6$ alkyl)$_2$, N$^+$(C$_1$-C$_6$ alkyl)$_3$, NH(C$_1$-C$_6$ alkaryl), N(C$_1$-C$_6$ alkaryl)$_2$, N$^+$(C$_1$-C$_6$ alkaryl)$_3$, NH(C$_5$-C$_{20}$ aryl), N(C$_5$-C$_{20}$ aryl)$_2$, (C$_1$-C$_6$)alkyl-N(C$_1$-C$_6$ alkyl)$_2$, (C$_1$-C$_6$)alkyl-NH(C$_1$-C$_6$ alkyl), (C$_1$-C$_6$)alkyl-O(C$_1$-C$_6$ alkyl), (C$_1$-C$_6$)alkyl-S(C$_1$-C$_6$ alkyl), OH, C$_1$-C$_6$ alkoxy, C$_1$-C$_6$ haloalkoxy, hydroxy(C$_1$-C$_6$ alkyl), hydroxy(C$_1$-C$_6$ alkaryl), hydroxy(C$_5$-C$_{20}$aryl), SH, S(C$_1$-C$_6$ alkyl), S(C$_1$-C$_6$ alkaryl), SOO(C$_5$-C$_{20}$aryl), SOO(C$_1$-C$_6$ alkyl), SOO(C$_1$-C$_6$ alkaryl), SOO(C$_5$-C$_{20}$aryl), hydroxy(C$_1$-C$_6$ alkoxy), alkoxy(C$_1$-C$_6$ alkyl), alkoxy(C$_1$-C$_6$ alkoxy), amino(C$_1$-C$_6$ alkyl), C$_1$-C$_6$ alkaryl, CONH$_2$, CONH(C$_1$-C$_6$ alkyl), CON(C$_1$-C$_6$ alkyl)$_2$, (C$_5$-C$_{20}$)aryl, (C$_5$-C$_{20}$)heteroaryl, CO$_2$H, C$_1$-C$_6$ alkyl-CO$_2$H, (C$_1$-C$_6$)alkyl-CO$_2$(C$_1$-C$_6$ alkyl), CO$_2$(C$_1$-C$_6$ alkyl), CO$_2$(C$_1$-C$_6$ alkaryl), CO$_2$(C$_1$-C$_6$ alkylheteroaryl), (C$_1$-C$_6$)alkyl-CO$_2$(C$_1$-C$_6$ alkaryl), (C$_1$-C$_6$)alkyl-CO$_2$(C$_1$-C$_6$ alkylheteroaryl), or any combination thereof. In some embodiments, the compound formed by the method of the invention is represented by Formulae 2b to 2y.

In some embodiments, the compound is represented by any of Formulae 2b-2d:

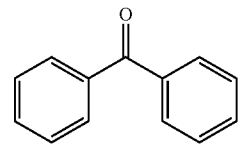

2b

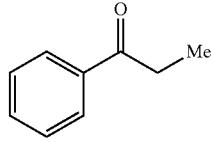

2c

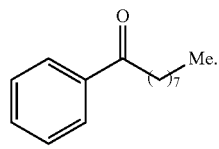
2d

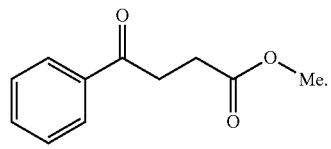
2k

In some embodiments, the compound is represented by any of Formulae 2e-2g:

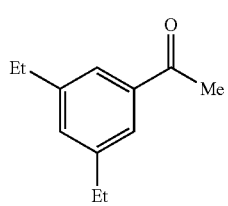
2e

In some embodiments, the compound is represented by any of Formulae 2l-2m:

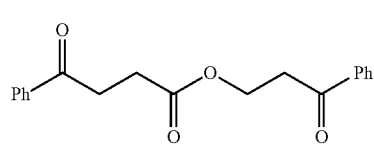
2l

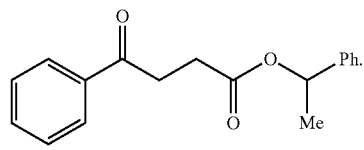
2m

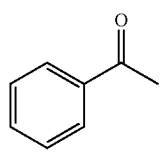
2f

In some embodiments, the compound is represented by any of Formulae 2n-2p:

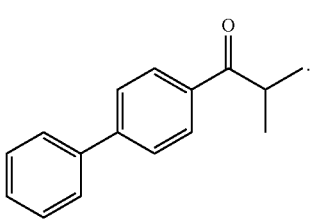
2g

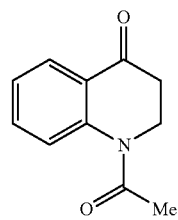
2n

In some embodiments, the compound is represented by any of Formulae 2h-2k:

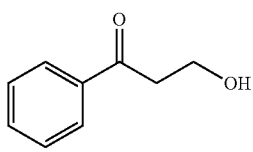
2h

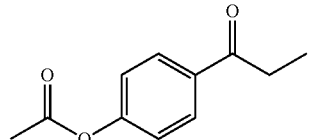
2o

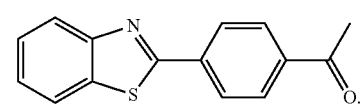
2p

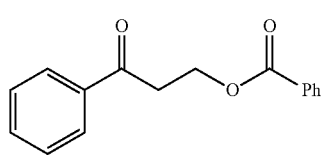
2i

In some embodiments, the compound is represented by any of Formulae 2r-2t:

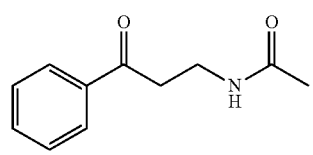
2j

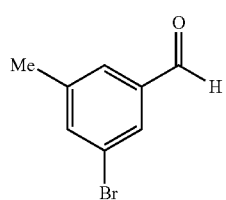
2r

-continued

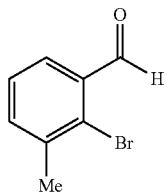

2s

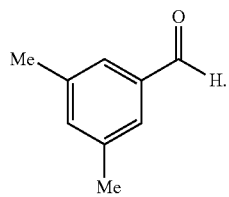

2t

In some embodiments, the compound is represented by any of Formulae 2u-2x:

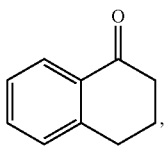

2u

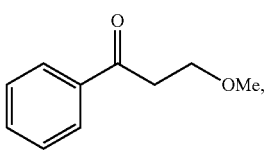

2v

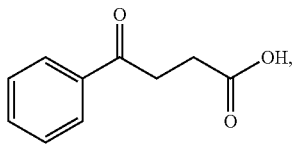

2w

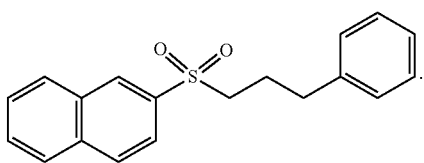

2x

In some embodiments, the compound is represented by Formula 2y:

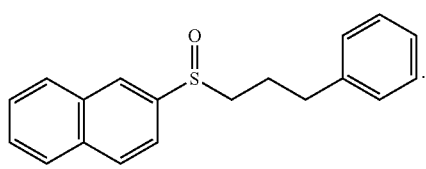 [SMILES: O=S(CCCc1ccccc1)c1ccc2ccccc2c1]

In some embodiments, the compound formed by the method of the invention is represented by Formula 3:

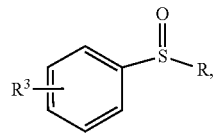

3 wherein R and W are as described herein.

In some embodiments, the compound formed by the method of the invention is represented by Formula 3a:

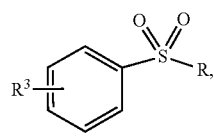

3a wherein R and $R^3$ are as described herein.

In some embodiments, the method comprises forming a sulfoxide-based compound of Formula 3 and/or a sulfone-based compound of Formula 3a by oxygenating a compound of Formula 1B3, wherein oxygenating is as described hereinabove.

In some embodiments, the compound formed by the method of the invention is represented by any of Formulae 3b.

In some embodiments, the method comprises excitation of an initiator. In some embodiments, the excitation is by an energy source. In some embodiments, the energy source is sufficient to provide an initiator to an excited state.

In some embodiments, the method of the invention comprises oxygenating a substrate of the invention by reacting the substrate with oxygen in the presence of an initiator, under appropriate conditions. In some embodiments, appropriate conditions comprise irradiating the substrate by electromagnetic radiation sufficient for excitation of an initiator of the invention. In some embodiments, appropriate conditions comprise irradiating the substrate via a light source. In some embodiments, appropriate conditions comprise irradiating a reaction mixture comprising the substrate. In some embodiments, appropriate conditions comprise irradiating a solution comprising the substrate. In some embodiments, appropriate conditions comprise irradiating a reactor comprising the reaction mixture, wherein irradiating is performed under appropriate conditions, as described herein.

In some embodiments, the method comprises exciting an initiator by an energy source (e.g. a light source) having an electromagnetic radiation dose in a range between 1 and 1000 mJ/cm$^2$, between 150 and 400 mJ/cm$^2$, between 50 and 150 mJ/cm$^2$, between 150 and 400 mJ/cm$^2$, between 200 and 400 mJ/cm$^2$, between 300 and 400 mJ/cm$^2$, between 1 and 10 mJ/cm$^2$, between 10 and 100 mJ/cm$^2$, between 100 and 1000 mJ/cm$^2$, including any range or value therebetween.

In some embodiments, the method comprises exciting an initiator by an energy source (e.g. a light source) having an energy of the emitted light of between 10 and 1000 W, between 10 and 50 W, between 50 and 100 W, between 100 and 200 W, between 200 and 300 W, between 300 and 500 W, between 500 and 1000 W, including any range or value therebetween.

The term "excited state" as used herein, is referred to a quantum state of a molecule, which has a higher energy than the ground state of the molecule.

In some embodiments, the energy source is at least one light source. In some embodiments, the light source generates light with a spectral range sufficient to excite an initiator. In some embodiments, the light source is used for photo-excitation of an initiator.

In some embodiments, the light source further comprises an optical filter. In some embodiments, the optical filter attenuates and/or retains at least a portion of the light spectrum.

In some embodiments, the light spectrum emitted by the light source has to be adjusted so as to match the absorption wavelength range of the initiator.

In some embodiments, at least a part of the spectral range overlaps the absorption wavelength of an initiator. In some embodiments, the light source generates light with a spectrum ranging from 200 to 900 nm, from 250 to 800 nm, from 250 to 500 nm, from 250 to 300 nm, from 250 to 350 nm, from 300 to 500 nm, from 300 to 400 nm, from 300 to 600 nm, from 300 to 700 nm, from 300 to 900 nm, including any range or value therebetween.

In some embodiments, the light source comprises: a sunlight, an artificial source of light or both. For example, a halogen lamp, or a LED device can be used as a light source. In some embodiments, the light source comprises a sunlight and an artificial source of light. In some embodiments, the light source comprises one or more artificial sources of light. In some embodiments, the light source is in communication with a processor.

In some embodiments, the light source is optically coupled to a reactor comprising a reaction mixture. In some embodiments, light emitted from the light source is transferred to the reactor by an optical fiber.

In some embodiments, the method comprises reacting the substrate with oxygen in the presence of an initiator. In some embodiments, the initiator generates a radical upon excitation by an energy source, wherein the energy source is as described hereinabove. In some embodiments, the initiator generates a plurality of radicals upon excitation by a light source, wherein the light source is as described hereinabove.

In some embodiments, the light source generates light in a spectral range above 200 nm, above 250 nm, above 300 nm, above 350 nm, above 400 nm, above 450 nm, above 500 nm, above 600 nm, above 700 nm, including any value therebetween.

In some embodiments, the light source generates a monochromatic light. In some embodiments, a wavelength of the monochromatic light is in a range between 200 nm and 900 nm, between 200 nm and 500 nm, between 300 nm and 500 nm, between 500 nm and 700 nm, between 700 nm and 900 nm, between 300 nm and 900 nm, including any range or value therebetween.

In some embodiments, the initiator generates a plurality of radicals upon excitation by light with a spectral range above 200 nm, above 250 nm, above 260 nm, above 270 nm, above 280 nm, above 290 nm, above 300 nm, above 310 nm, above 320 nm, above 330 nm, above 340 nm, above 350 nm, including any value therebetween. In some embodiments, the initiator generates a plurality of radicals upon excitation by light with a spectral range between 200 nm and 900 nm, between 200 nm and 300 nm, between 300 nm and 400 nm, between 300 nm and 350 nm, between 250 nm and 350 nm, between 200 nm and 500 nm, between 350 nm and 400 nm, between 400 nm and 500 nm, between 300 nm and 500 nm, between 500 nm and 700 nm, between 700 nm and 900 nm, between 300 nm and 900 nm, between 900 nm and 1500 nm, including any range or value therebetween.

In some embodiments, the light is a sunlight. In some embodiments, the light source is a LED. In some embodiments, the light source comprises an array comprising a plurality of LEDs. In some embodiments, the light source comprises a plurality of light sources.

Non-limiting examples of radicals include but are not limited to: a halogen radical (e.g., Br-, Cl-, F-radical), and a hydroxy radical or any combination thereof. In some embodiments, the radical is a halogen radical. In some embodiments, the radical is a bromine radical. In some embodiments, the radical formed by an excited initiator is devoid of singlet oxygen. In some embodiments, the radical is devoid of superoxide. In some embodiments, the initiator is capable of generating one or more radicals upon excitation by an energy source, wherein the energy source and the one or more radicals are as described herein.

In some embodiments, the radical has a reactivity sufficient to react with the substrate. In some embodiments, the radical has a reactivity sufficient to abstract a hydrogen radical, thereby forming a benzyl radical of the substrate. In some embodiments, the initiator is capable of reacting with the substrate upon excitation of the initiator by an energy source, thereby forming a benzyl radical of the substrate. In some embodiments, the initiator is capable of reacting with the substrate, so as to result in a formation of a benzyl radical of the substrate. In some embodiments, the benzyl radical has a sufficient reactivity so as to form endoperoxide 7 upon reaction with oxygen, as shown hereinbelow by Scheme 3 (see FIG. 2). In some embodiments, the initiator has a sufficient reactivity so as to promote formation of endoperoxide 7 upon reaction of the substrate with oxygen, as shown hereinbelow by Scheme 3 (see FIG. 2).

In some embodiments, an initiator comprises a photoreactive molecule. In some embodiments, an initiator is a photosensitizer. In some embodiments, an initiator is a pre-catalyst. In some embodiments, an initiator initiates a radical reaction. In some embodiments, an initiator initiates a radical formation.

In some embodiments, the initiator is represented by Formula 4:

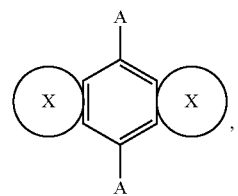

wherein: each X is as described hereinabove, or is absent; and each A independently represents a halo group.

In some embodiments, each X independently comprises an aryl (optionally substituted by one or more R) or is absent. In some embodiments, each X independently comprises a C3-C10 cycloalkane.

In some embodiments, wherein the aryl is selected from the group consisting of: an aromatic ring, a fused aromatic ring, and a substituted aromatic ring or a combination thereof.

In some embodiments, the initiator is represented by Formula 4a:

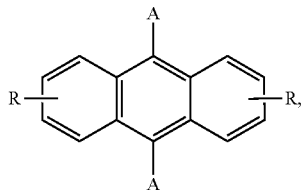

wherein A and R are as described hereinabove, or wherein R is absent. In some embodiments, the initiator comprises a plurality of compounds represented by Formulae 4 or 4a.

In some embodiments, at least one A is bromo. In some embodiments, the initiator comprises 9,10-dibromoanthracene.

In some embodiments, the initiator (such as 9,10-dibromoanthracene) is a photosensitizer.

In some embodiments, the initiator is $CBr_4$ (carbon tetrabromide). In some embodiments, $CBr_4$ forms a bromine radical upon irradiation by a light source having a spectral range as described hereinabove. In some embodiments, the initiator induces a bromine radical formation, and subsequently initiates a radical reaction.

In some embodiments, the method comprises reacting the substrate with oxygen in the presence of excited $CBr_4$, thereby forming a hydroperoxide (FIG. 1). In some embodiments, the substrate comprises a tertiary benzylic carbon.

In some embodiments, the initiator is substantially devoid of an additional reactive compound. In some embodiments, the initiator is substantially devoid of a metal (e.g. a transition metal catalyst, such as Cu, Ru, Pt, Au, Pd, Ir etc. including any salt of any complex thereof). In some embodiments, the initiator is a non-metallic initiator. In some embodiments, the initiator is substantially devoid of acridine or a derivative thereof (such as 9-mesityl-10-methylacridinium). In some embodiments, the initiator is substantially devoid of eosin Y. In some embodiments, the initiator is substantially devoid of anthraquinone, or a derivative thereof, such as carboxy-anthraquinone. In some embodiments, the initiator is substantially devoid of anthracene.

In some embodiments, the initiator is a non-radical initiator. In some embodiments, the initiator is substantially devoid of a radical. In some embodiments, the initiator is substantially devoid of an additional photoreactive molecule. In some embodiments, the initiator is substantially devoid of a radical initiator. Various radical initiators are well-known in the art, such as AIBN and peroxides (e.g. benzoyl peroxide and peroxydisulfate). In some embodiments, the initiator is substantially devoid of N-hydroxysuccinimide. In some embodiments, the initiator is substantially devoid of N-hydroxyphthalimide. In some embodiments, the initiator is substantially devoid of a halogen (such as bromine or chlorine gas). In some embodiments, the initiator is substantially devoid of N-Bromophthalimide or N-Chlorophthalimide. In some embodiments, the initiator is substantially devoid of n-bromosuccinimide or n-chlorosuccinimide. In some embodiments, the initiator is substantially devoid of carbontetrachloride. In some embodiments, the initiator is substantially devoid of carbontetrabromide. In some embodiments, substantially is as described hereinbelow.

In some embodiments, the initiator consists essentially of one or more compounds of Formula 4 and/or of Formula 4a.

In some embodiments, at least 90%, at least 91%, at least 92%, at least 93%, at least 94%, at least 95%, at least 96%, at least 97%, at least 98%, at least 99%, at least 99.5%, at least 99.9% by weight of the initiator consists of one or more compounds of Formula 4 and/or of Formula 4a.

In some embodiments, the method of forming an oxygenated benzylic C—H bond comprises a reaction illustrated by any one of: Scheme 1, and Scheme 2.

Without being limited to any particular theory or mechanism, provided herein (Scheme 3) an exemplary reaction mechanism for the free radical formation of any one of the compounds represented by Formulae 1a, 1b, and 2.

Figure 2:
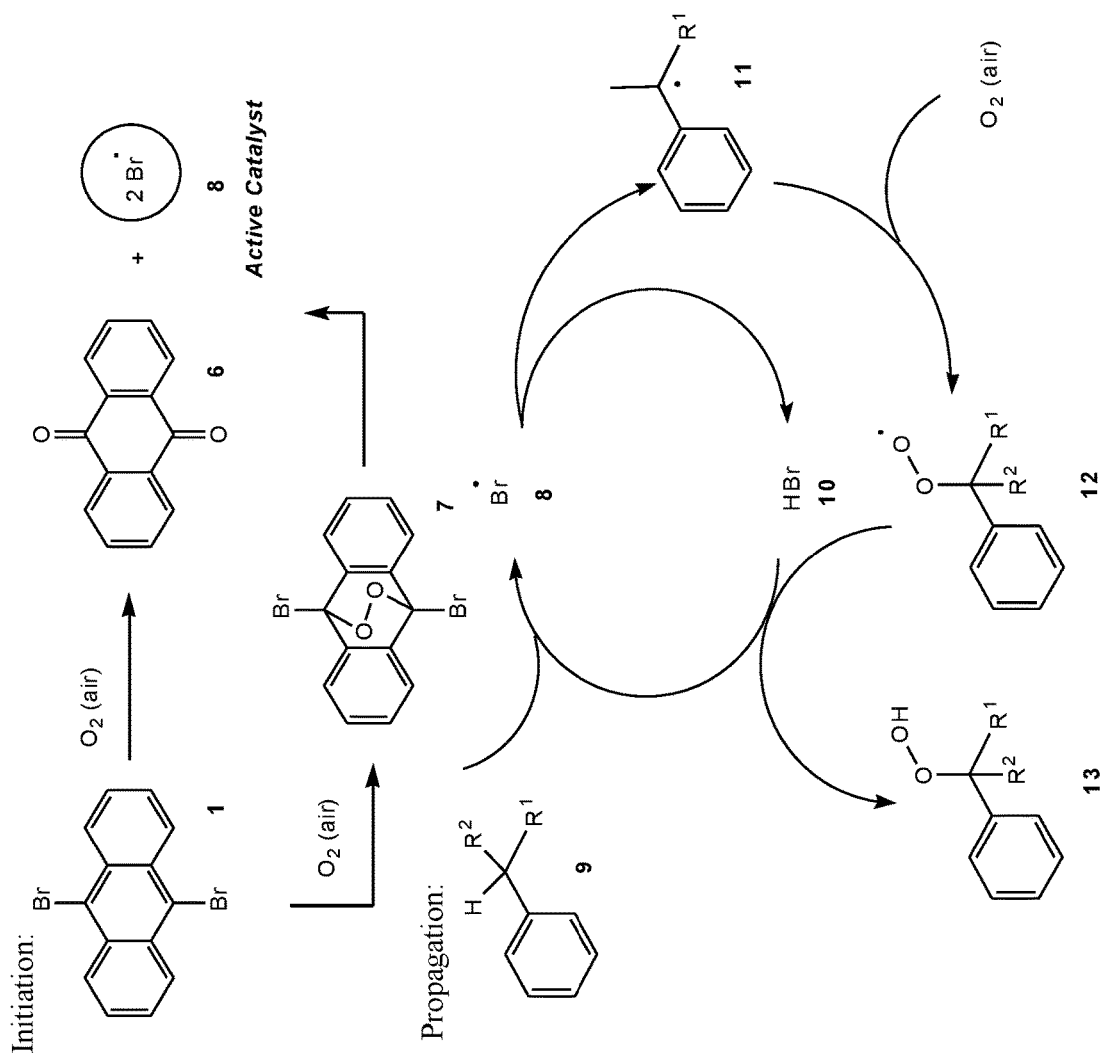
FIG. 2 is a scheme (also referred to herein as Scheme 3) showing an exemplary unlimiting mechanism for the free radical formation of peroxides (13) and ketones (14).
Figure 2:
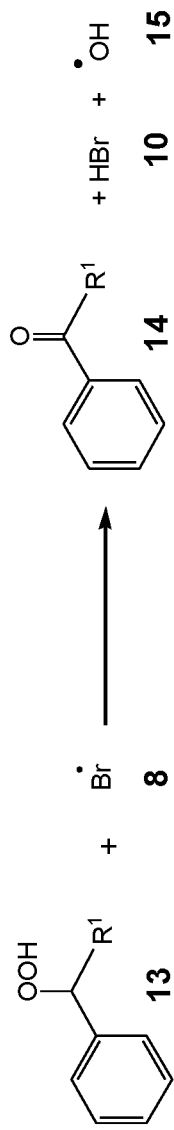

Reference is now made to FIG. 2, showing an exemplary mechanism for the free radical formation of peroxides (13) and ketones (14).

An exemplary mechanism with an exemplary initiator (9,10-dibromo anthracene) as illustrated by Scheme 3 (see FIG. 2) comprises the stages: 1) Initiation, 2) Propagation and optionally 3) Further propagation (for primary and secondary benzylic carbons).

The initiation pathway involves singlet oxygen formation by photo-induced excitation of the initiator (e.g. 9,10-dibromo anthracene) 1 and subsequent interaction of the excited initiator with oxygen, thereby forming a singlet oxygen. Then, singlet oxygen may react with the initiator by a cycloaddition, followed by formation of endoperoxide 7. This endoperoxide dissociates to give anthraquinone 6 and two equivalents of bromine radical 8.

Subsequently, in the propagation cycle radical 8 abstracts a hydrogen atom from the substrate 9 at the benzylic position to afford HBr 10 and carbon-centred radical 11. Fast reaction of 11 with oxygen gives peroxyl radical 12 which then abstracts H· from HBr 10 to regenerate bromine radical 8 that continues the chain until substrate 9 is consumed. Alternatively, the peroxyl radical 12 may serve to abstract a hydrogen atom from the starting material. In the case the substrate is a tertiary benzylic carbon such as cumene, the resulting product 3 is cumene hydroperoxide.

In the case of a secondary benzylic carbon, carrying an additional hydrogen atom, abstraction of a second hydrogen atom may take place with concomitant cleavage of the weak peroxide bond leading to the observed product ketone 14 and a hydroxy radical 15 (Further propagation stage). The hydroxy radical 15 may then also serve as a hydrogen abstractor from 9 or 13, with formation of water.

In some embodiments, the method comprises mixing the substrate and the initiator with a solvent, thereby forming a reaction mixture. In some embodiments, the reaction mixture is formed prior to the photo-induced initiation stage.

In some embodiments, the molar concentration of the substrate within the reaction mixture is in a range from 0.01 to 2 mol/L, from 0.01 to 0.02 mol/L, from 0.02 to 0.03 mol/L, from 0.03 to 0.04 mol/L, from 0.04 to 0.05 mol/L, from 0.05 to 0.06 mol/L, from 0.06 to 0.08 mol/L, from 0.08 to 0.1 mol/L, from 0.1 to 0.2 mol/L, from 0.2 to 0.4 mol/L, from 0.4 to 0.6 mol/L, from 0.6 to 0.8 mol/L, from 0.8 to 1 mol/L, from 1 to 1.2 mol/L, from 1.2 to 1.4 mol/L, from 1.4 to 1.6 mol/L, from 1.6 to 1.8 mol/L, from 1.8 to 2 mol/L, including any range therebetween.

In some embodiments, the molar ratio of the substrate to the initiator within the reaction mixture from is at least 1:0.01, at least 1:0.04, at least 1:0.06, at least 1:0.08, at least 1:0.1, at least 1:0.15, at least 1:0.2, at least 1:0.3, at least 1:0.5, including any value therebetween.

In some embodiments, the molar ratio of the substrate to the initiator within the reaction mixture from is in a range from 1:0.01 to 1:0.5, from 1:0.01 to 1:0.05, from 1:0.05 to 1:0.1, from 1:0.1 to 1:0.2, from 1:0.2 to 1:0.5, including any range therebetween.

In some embodiments, the solvent is characterized by a sufficient oxygen solubility and inertness to the reaction conditions (e.g., radicals, singlet oxygen).

Non-limiting examples of appropriate solvents for the reaction include but are not limited to: acetonitrile, n-butyronitrile, iso-butyronitrile, acetone, methyl-ethyl ketone, hydrocarbons (e.g. hexane, pentane, cyclohexane) or any combination thereof.

In some embodiments, the solvent comprises acetonitrile. In some embodiments, the solvent comprises a mixture of acetonitrile and an additional organic solvent.

The selection of the appropriate solvent for the reaction depends upon a variety of aspects, known to those skilled in the art. Some exemplary aspects are: solubility (of both oxygen and the substrate), cost efficiency, recycling, and toxicity.

In some embodiments, the method is executed under conditions sufficient for the compound formation. The terms "compound" and "product" are used herein interchangeably. Exemplary methods are described in greater detail in Example 1. Additional methods are described hereinabove.

In some embodiments, the conditions are selected so as to provide an optimal yield of the product. In some embodiments, the conditions are selected so as to result in an almost complete conversion of the substrate. In some embodiments, the conditions are optimized with respect to any of: concentration of the reactants, reaction temperature, and reaction time, thereby resulting in maximum product yield.

In some embodiments, the conditions are selected so as to result in a reaction with high selectivity. As used herein, the term "selectivity" is related to a dominant reactivity of the radical species towards the benzylic C—H bond, and on the same time a negligible reactivity of the radical species towards other functional groups. The selectivity of the reaction has to be sufficient to minimize by-product formation. In some embodiments, the selectivity comprises a dominant formation of a product of the invention (e.g. a carbonyl-based compound or the hydroperoxide-based compound of the invention). In some embodiments, the selectivity comprises a dominant formation of a sulfone-based product of the invention over benzylic carbonyl and/or benzylic hydroperoxide.

In some embodiments, the reaction is characterized by selectivity of at least 60%, at least 70%, at least 75%, at least 80%, at least 85%, at least 90%, at least 95%, at least 97%, at least 99%, including any range therebetween.

In some embodiments, the reaction is characterized by selectivity and by high yield of the desired oxygenated compound of the invention. In some embodiments, the reaction yield is between 30 and 99%, between 30 and 50%, between 50 and 70%, between 70 and 75%, between 75 and 80%, between 80 and 85%, between 85 and 90%, between 90 and 95%, between 95 and 99%, including any range therebetween.

In some embodiments, the reaction is characterized by selectivity and by high conversion of the substrate. In some embodiments, high conversion comprises at least 80%, at least 85%, at least 90%, at least 95%, at least 97%, at least 99%, including any range therebetween.

Surprisingly, the inventors found, that the initiator of the invention is superior to singlet oxygen forming initiators (e.g. a photosensitizer such as anthraquinone), with respect to reaction selectivity and/or substrate conversion.

In some embodiments, conditions sufficient to form the compound disclosed herein are optimized conditions. In some embodiments, the method of the invention provides optimized condition, thus resulting in high reaction selectivity and a high product yield, as shown in FIG. 1.

In some embodiments, appropriate conditions comprise a temperature in a range from 0 to 100° C., from 10 to 20° C., from 20 to 25° C., from 25 to 30° C., from 30 to 35° C., from 35 to 40° C., from 40 to 50° C., from 50 to 60° C., from 60 to 70° C., from 70 to 100° C., including any range therebetween. In some embodiments, the temperature is less than 40° C., than 38° C., than 35° C., than 30° C., than 25° C., than 20° C., including any range therebetween. In some embodiments, the temperature is less than 35° C.

In some embodiments, appropriate conditions comprise a molar ratio between the initiator and the substrate (e.g. a compound of any one of Formulae 1A1, 1B1, 1B2, and 1B3) being between 1 and 30 mol %, 1 and 5 mol %, 5 and 7 mol %, 7 and 10 mol %, 10 and 12 mol %, 12 and 15 mol %, 15 and 20 mol %, 20 and 30 mol %, including any range therebetween. In some embodiments, appropriate conditions comprise a molar ratio between the initiator and the substrate being between 8 and 12 mol %. In some embodiments, sufficient conditions comprise a molar ratio between the initiator and the substrate being between 9 and 11 mol %.

In some embodiments, appropriate conditions comprise a reaction time in a range from 1 to 40 h, from 1 to 2 h, from 2 to 3 h, from 3 to 4 h, from 4 to 6 h, from 6 to 10 h, from 10 to 20 h, from 20 to 30 h, from 30 to 40 h, including any range therebetween.

In another aspect of the invention, provide herein a compound synthesized by the method of the invention. In some embodiments, the compound comprises a trace amount of the initiator of the invention. In some embodiments, the compound comprises a trace amount of anthracene. In some embodiments, the compound is cumene. In some embodiments, the compound is any one of the compounds 2b to 2y.

In some embodiments, the compound comprises a trace amount of anthracene and of the initiator of the invention. Us used herein the term "trace amount" refers to an unsignificant amount of a compound (e.g. impurity) within the end product, such as from 1 ppm to 2%, from 1 ppm to 10 ppm, from 10 ppm to 100 ppm, from 100 ppm to 0.1%, from 0.1% to 1%, from 1 to 2%, including any range therebetween.

General

As used herein the term "about" refers to ±10%.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

In some embodiments, the term "consisting essentially of" refers to at least 80%, at least 85%, at least 90%, at least 95%, at least 97%, at least 98%, at least 99%, at least 99.5%, at least 99.9%, by weight of the dry content of the compound (e.g. the substrate or the initiator) of the invention.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

As used herein, the term "substantially" is at least 80%, at least 90%, at least 92%, at least 95%, at least 97%, at least 98%, at least 99% by weight of the composition including any range or value therebetween.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As used herein, the term "alkyl" describes an aliphatic hydrocarbon including straight chain and branched chain groups. The alkyl group has 1 to 100 carbon atoms, and more preferably 1-50 carbon atoms. Whenever a numerical range; e.g., "1-100", is stated herein, it implies that the group, in this case the alkyl group, may contain 1 carbon atom, 2 carbon atoms, 23 carbon atoms, etc., up to and including 100 carbon atoms. In the context of the present invention, a "long alkyl" or "high alkyl" is an alkyl having at least 10, or at least 15 or at least 20 carbon atoms in its main chain (the longest path of continuous covalently attached atoms), and may include, for example, 10-100, or 15-100 or 20-100 or 21-100, or 21-50 carbon atoms. A "short alkyl" or "low alkyl" has 10 or less main-chain carbons. The alkyl can be substituted or unsubstituted, as defined herein.

The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" or "cycloalkane" describes an all-carbon monocyclic or fused ring (i.e., rings that share an adjacent pair of carbon atoms) group where one or more of the rings does not have a completely conjugated pi-electron system. The cycloalkyl group may be substituted or unsubstituted, as indicated herein.

The term "aryl" or "aromatic" describes an all-carbon monocyclic or fused-ring polycyclic (i.e., rings which share adjacent pairs of carbon atoms) groups having a completely conjugated pi-electron system. The aryl group may be substituted or unsubstituted, as indicated herein. In some embodiments, the aryl group may be substituted by one or more (e.g. 2, 3, 4 or 5) of R, wherein R is as described herein.

The term "alkoxy" describes both an —O-alkyl and an —O-cycloalkyl group, as defined herein.

The term "aryloxy" describes an —O-aryl, as defined herein.

Each of the alkyl, cycloalkyl and aryl groups in the general formulas herein may be substituted by one or more substituents, whereby each substituent group can independently be, for example, halide, alkyl, alkoxy, cycloalkyl, alkoxy, nitro, amine, hydroxyl, thiol, thioalkoxy, thiohydroxy, carboxy, amide, aryl and aryloxy, depending on the substituted group and its position in the molecule. Additional substituents are also contemplated.

The term "halide", "halogen" or "halo group" describes fluorine, chlorine, bromine or iodine.

The term "hydroxyl" or "hydroxy" describes a —OH group.

The term "thiohydroxy" or "thiol" describes a —SH group.

The term "thioalkoxy" describes both an —S-alkyl group, and a —S-cycloalkyl group, as defined herein.

The term "thioaryloxy" describes both an —S-aryl and a —S-heteroaryl group, as defined herein.

The term "amine" describes a —NR'R" group, with R' and R" as described herein.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

The term "heteroalicyclic" or "heterocyclyl" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofuran, tetrahydropyrane, morpholino and the like.

The term "carboxy" or "carboxylate" describes a —C(=O)—OR' group, where R' is hydrogen, alkyl, cycloalkyl, alkenyl, aryl, heteroaryl (bonded through a ring carbon) or heteroalicyclic (bonded through a ring carbon) as defined herein.

The term "carbonyl" describes a —C(=O)—R' group, where R' is as defined hereinabove.

The above-terms also encompass thio-derivatives thereof (thiocarboxy and thiocarbonyl).

The term "thiocarbonyl" describes a —C(=S)—R' group, where R' is as defined hereinabove.

A "thiocarboxy" group describes a —C(=S)—OR' group, where R' is as defined herein.

A "sulfinyl" group describes an —S(=O)—R' group, where R' is as defined herein.

A "sulfonyl" or "sulfonate" group describes an —S(=O)$_2$—R' group, where Rx is as defined herein.

A "carbamyl" or "carbamate" group describes an —OC(=O)—NR'R" group, where R' is as defined herein and R" is as defined for R'.

A "nitro" group refers to a —NO2 group.

A "cyano" or "nitrile" group refers to a —C≡N group.

As used herein, the term "azide" refers to a —N$_3$ group.

The term "sulfonamide" refers to a —S(=O)$_2$—NR'R" group, with R' and R" as defined herein.

The term "phosphonyl" or "phosphonate" describes an —O—P(=O)(OR')2 group, with R' as defined hereinabove.

The term "phosphinyl" describes a —PR'R" group, with R' and R" as defined hereinabove.

The term "alkaryl" describes an alkyl, as defined herein, which substituted by an aryl, as described herein. An exemplary alkaryl is benzyl.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. In some embodiments, the heteroaryl group may be substituted by one or more (e.g. 2, 3, 4 or 5) of R, wherein R is as described herein. Representative examples are thiadiazole, pyridine, pyrrole, oxazole, indole, purine and the like.

The term "haloalkyl" describes an alkyl group as defined above, further substituted by one or more halide(s).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Materials and Methods

Experimental procedures: Standard inert atmosphere techniques were used in handling all air and moisture sensitive reagents. Reactions were carried out under an N2 atmosphere in oven-dried glassware (temp of oven kept at 100-120° C.). All required solvents were dried according to standard procedures and techniques before use. Room temperature refers to 28-30° C. and the actual temperature of the reaction is mention in the synthetic procedure. Bulk solutions were evaporated under reduced pressure using a rotary evaporator.

Reactions were monitored by thin-layer chromatography (TLC Silica gel 60 F254 from Merck), visualized under dual short/long wave UV fluorescence (λ max=254 and 365 nm) and developed with Iodine and KMnO4 stains, followed by heating if necessary.

Column chromatography was performed on silica (230-400 mesh size). Melting Points were measured on a Stuart melting point instrument and are uncorrected. Fourier transform infrared (FT-IR) spectra were taken on a Bruker Optics ALPHA-E spectrometer with a universal Zn—Se ATR (attenuated total reflection) accessory in the 600-4000 cm-1 region.

NMR spectroscopy: 1H NMR spectroscopy measurements were carried out on Bruker 400 MHz NMR spectrometer with CDCl$_3$ (δ 7.26) as an internal standard unless otherwise stated. The 13C NMR spectra were recorded at 101 MHz with CDCl$_3$ (δ 77.16) as an internal standard unless otherwise stated. Chemical shifts (δ) are given in ppm downfield from TMS and coupling constants (J) are in Hertz (Hz).

The 1H NMR spectra are reported as follows: δ/ppm (multiplicity, coupling constant followed by the number of protons). Multiplicity of 1H NMR is abbreviated as follows: s=singlet, d=doublet, dd=doublet of doublets, t=triplet, dt=doublet of triplet, q=quartet, dq=doublet of quartet, m=multiplet.

HR Mass Spectrometry: High-resolution mass spectra were recorded by the MS service at Technion. ESI-MS (m/z): was recorded on a Waters Micromass LCT premier instrument at 70 eV in the positive or negative mode. APCI was recorded on a Bruker Impact II instrument.

Example 1

Benzylic sp$^a$ C—H Oxygenation for the Formation of Hydroperoxide-Based Compounds General Procedure a for the Oxygenation of Cumene and Derivatives (Results Summarized in FIG. 1):

In an oven dried 100 mL photochemical flask were added 1.0 mmol (0.12 g, 0.14 mL) cumene and 9,10-dibromoanthracene (10 mol %, 0.034 g). 25 mL of acetonitrile were added, and the solution was stirred exposed to sun light and atmospheric air for the stated number of hours. The progress of the reaction was monitored by thin layer chromatography (TLC). The conversion and the ratio of the products was determined by $^1$H NMR. Exemplary conversion ratios and yields are represented in Table 1.

General Procedure C for sp$^a$ C—H Oxidation Using Blue LED (Compounds 2u, 2g, 2j, 2m, 2l, 2o, 2p):

In an oven dried flask, substrate (1 mmol, 1.0 equiv.) and 9,10-dibromoanthracene (0.1 equiv.) was dissolved in 25 mL acetonitrile. The solution was stirred exposed to light from a blue LED while open to air at room temperature. The temperature was generally 15-20° C. The reaction was monitored by TLC.

After completion of reaction the mixture was optionally purified by column chromatography (under standard separation conditions) to afford the corresponding products.

It was found that that 9,10-dibromo-anthracene serves as an efficient initiator for the reaction using a Pyrex vessel (which filtered light with a cut-off at 330 nm) solar light or a LED lamp. (Table 1, entry 1). Initially, the inventors surveyed a range of radical initiators or reagents including N-bromo- and N-chloro succinimide, nitroxides, and CCl$_4$ in combination with various amines to give charge transfer complexes. None of these initiator systems afford cumene hydroperoxide in any appreciable amount. In addition, the formation of cumene hydroperoxide is invariably accompanied by the formation of other typical cumene hydroperoxide side products such as acetophenone (5) and 2-phenyl-2-propanol (4).

Ten mol % of 9,10-dibromo anthracene leads to the cleanest and most efficient conversion. Under these conditions, 93% of cumene (2) is converted affording cumene hydroperoxide (3) in >87% yield along with 10% of 2-phenyl-2-propanol (4) and 4% of acetophenone (5) (Table 1, entry 1, yields determined by the ratio of products and starting materials all of which are known). Lower amounts of 9,10-dibromo-anthracene (Table 1, entry 2) leads to incomplete conversion of cumene (1) under otherwise identical conditions (Table 1, entry 2 and entry 3).

Optimization of the conditions showed that acetonitrile, well known for the relatively high solubility of oxygen therein, can be considered as a preferable solvent for the reaction. Doubling the concentration led to lower conversion cumene (Table 1, entry 4). Extending the reaction time to 9 hours brings about 95% conversion of cumene, but also higher formation of acetophenone (Table 1, entry 6). Using a Blue LED lamp as the visible light source comparable results are achieved in 8 hours (Table 1, entry 5), but with slightly higher amounts of acetophenone than the conditions in entry 1.

Isolation of 9,10-anthraquinone from the reaction mixture indicates that 9,10-dibromo-anthracene acts as an initiator rather than a catalyst. However, replacing 9,10-dibromo anthracene with 9,10-anthraquinone, a well-known sensitizer for singlet oxygen formation, results in formation of 2-phenyl-2-propanol (4) and acetophenone (5) as the major products (Table 1, entry 7).

Attempting to avoid singlet oxygen formation by anthraquinone, which absorbs mainly below 360 nm, a reaction was carried out using a glass filter with a cut-off frequency of 360 nm. However, under these conditions reaction rate drops and only 53% conversion is reached in 18 h (Table 1, entry 8). Alternatively, the anthraquinone can be easily reconverted to 9,10-dibromo anthracene by a well-known synthetic procedure.

No reaction takes place in the absence of a light source (Table 1, entry 9). When the reaction was kept in the dark following 4 hours of light exposure very little conversion took place in the dark (Table 1, entry 10).

Furthermore, 10 mol % of initiator is needed for high conversion of cumene and that 5 or 7 mol % lead to incomplete reaction (Table 1, entry 2 and 3). In the absence of 9,10-dibromo-anthracene (Table 1, entry 11) no formation of cumene hydroperoxide (3, R=H) takes place. It is postulated, that an indication of a radical reaction is an experiment carried out in the presence of 10 mol % TEMPO (Table 1, entry 12). TEMPO is a nitroxide that would react readily with a bromine radical 8 or carbon centered radicals such as 11 (Scheme 3) thereby inhibiting a radical chain reaction. Indeed, in this reaction no reaction takes place despite the possible formation of two Br radicals from 9,10-dibromoanthracene (as shown in Scheme 3). Adding additional HBr (10 mol %) to the reaction had little effect although more decomposition of the hydroperoxide 3 (R=H) to give acetophenone 5 (R=H) and alcohol 4 (R=H) took place (Table 1, entry 13).

Adding varying amounts of NHPI, did not afford any advantage nor did it inhibit the reaction (see Table 1, entry 1 versus entry 14 and 15). As always scaling up is the Achilles heel of photochemical reactions. When the reaction was run on 1.2 gram scale in a 500 mL Pyrex vessel the conversion dropped to only 14%. From this experiment were isolated recovered initiator (41% isolated yield) along with anthraquinone (47%). We therefore carried out this experiment using blue LED (Table 1, entry 16). The reaction required 33 h to reach 93% conversion and gave a 47 to 21 to 32 ratio of hydroperoxide 3 (R=H), alcohol 4 (R=H), and acetophenone 5 (R=H).

As a preliminary investigation of the influence of electron donating and—withdrawing substituents on the reaction the inventors tested 1-isopropyl-4-methoxybenzene (2, R=OMe) and 1-chloro-4-isopropylbenzene (2, R=Cl) as substrates in the reaction (Table 1, entries 17-19). 1-Isopropyl-4-methoxybenzene (2, R=OMe) gave p-methoxy-acetophenone 5 (R=OMe) as the only product after 7 hours of irradiation (Table 1, entry 18). No starting material remained. To test whether this was due to decomposition of an intermediate hydroperoxide the reaction was therefore also run for 4 h. Interestingly, in this experiment 89% of starting 1-isopropyl-4-methoxybenzene (2, R=OMe) had reacted to give the corresponding hydroperoxide 3 (R=OMe) and p-methoxy-acetophenone 5 (R=OMe) in a 46 to 56 ratio (Table 1, entry 17). This shows clearly that a major part or all of ketone 5 (R—OMe) is formed from hydroperoxide 3 (R=OMe). In contrast 1-chloro-4-isopropylbenzene (2, R=Cl) reacted in a manner similar to cumene (2, R=H). Thus, after 9 hours of irradiation under standard conditions 95% conversion was achieved. The hydroperoxide 3 (R=Cl), alcohol 4 (R=Cl) and ketone 5 (R=Cl) formed in a 77 to 4 to 16 ratio (Table 1, entry 19). The numbers (3, 4, 5) represent compounds as depicted in FIG. 1.

Example 2

Benzylic C—H Oxygenation for the Formation of Carbonyl-Based Compounds

General Procedure B for Benzylic C—H Oxygenation Using Sunlight (Compounds 2b to 2f, 2h, 2i, 2k, 2n, 2r to 2t, 2v, and 2y):

In an oven dried flask, substrate (1 mmol, 1.0 equiv.) and 9,10-dibromoanthracene (0.1 equiv.) was dissolved in 25 mL acetonitrile. The solution was stirred exposed to sun light while open to air. The internal temperature was 32-35° C. The reaction was monitored by TLC. After completion of reaction, the mixture was transferred to 50 mL round bottom flask and concentrated under reduced pressure. To the concentrated reaction mixture 30 mL of ethyl acetate was added. The organic layer was washed with saturated NaHCO$_3$ solution (10 mL), dried (Na$_2$SO$_4$), and concentrated under reduced pressure. The crude product was purified by column chromatography (2→50% EtOAc in n-hexane) to afford the corresponding products.

General Procedure C for Benzylic C—H Oxygenation Using Blue LED:

In an oven dried flask, substrate (1 mmol, 1.0 equiv.) and 9,10-dibromoanthracene (0.1 equiv.) was dissolved in 25 mL acetonitrile. The solution was stirred exposed to light from a blue LED while open to air at room temperature. The temperature was generally 15-20° C. The reaction was monitored by TLC. After completion of reaction, the mixture was transferred to 50 mL round bottom flask and concentrated under reduced pressure. To the concentrated reaction mixture 30 mL of ethyl acetate was added. The organic layer was washed with saturated NaHCO$_3$ solution (10 mL), dried (Na$_2$SO$_4$), and concentrated under reduced pressure. The crude product was purified by column chromatography (2→50% EtOAc in n-hexane) to afford the corresponding products.

The inventors investigated the synthesis of benzylic ketones from a series of functionalized secondary alkylbenzenes substrates in order to outline scope and functional group selectivity (see Formulae 2b to 2y). Generally, the ketones where formed cleanly and as expected no residual hydroperoxide intermediate products could be observed. Running the reaction at ambient temperature is an advantage of this protocol as it precludes the thermal cleavage of the weak peroxyl bond of the intermediate hydroperoxide 13, so as to form alcohol-based side-products.

The inventors investigated both the use of blue LED light and solar light. For both light sources, the reactions are very clean with the balance of product simply being recovered starting material i.e. the yield is approximate also the conversion percentage and higher yields can be achieved simply by extending the light exposure time.

Simple alkylbenzenes such as diphenyl-methane, 1-phenyl-propane, and nonyl-benzene cleanly give the ketones respectively. There appears to be no discernible rate difference for products using solar light or LED. Reaction using LED were generally run indoors at 15-20° C. while the reactions run outside under solar light exposure typically reached 32-35° C. internal temperature.

In the case of 1,3,5-triethylbenzene only a single product, was isolated in 62% yield after 9 hours in the sun. Tetrahydronaphthalene affords the carbonyl compound in 70% isolated yield after 14 hours of irradiation with a blue LED lamp. Reaction remains selective for the benzylic position in the presence of a branched chain resulting in a product in 72% yield after 11 hours (LED).

The inventors investigated the presence of functional groups in the alkyl-sidechain. Reaction of 1-phenyl ethane afforded acetophenone in 91% isolated yield after only 8 hours of irradiation (LED). 1-hydroxy-3-phenyl-propane cleanly affords a corresponding ketone in 38% yield after 9 hours irradiation. In comparison with simple 1-phenyl-propane the reaction is considerably slower. It was speculated that this is due to less efficient diffusion due to hydrogen bonding. Indeed, when the alcohol is replaced with an ester the rate and conversion increased and corresponding carbonyl was isolated in 61% yield after 10 hours. The same could be observed for the analogous methyl ether, which gave the corresponding carbonyl in 62% yield after 9 hours. When the analogous acetamide is used the conversion rate again dropped and the corresponding carbonyl is isolated in 81% yield after 33 hours of LED irradiation. In contrast, the oxidation of 4-phenyl-butanoic acid gave the corresponding carbonyl in 59% yield after 9 hours.

Selectivity is also observed for 4-phenyl-butanoic acid methyl ester which affords 2k in 58% isolated yield after 14 hours solar light irradiation. An amide nitrogen is also tolerated in 1-(3,4-dihydroquinolin-1(2H)-yl)ethan-1-one, which affords 2n in 64% yield. In contrast, when two different benzylic positions were present, one simple and one alkoxy, the desired product, 2m was isolated in 54% yield alongside about 30% acetophenone and other unidentified decomposition products. Two different benzylic position may be oxidized simultaneously to give diketone 2l in 68% yield after 28 hours LED irradiation. Substitution in the aromatic ring is well tolerated. For example, 4-acetoxy-1-propyl-benzene reacts cleanly to give 2o in 62% yield after 16 hours (LED). A heteroaromatic group as in 2p is also tolerated. This is important for pharmaceutical applications.

Interestingly sulfides undergo oxidation to the sulfone via the sulfoxide rather than benzylic oxidation as may be seen for products 2x (79% yield) isolated together with its sulfoxide 2y which was isolated in 12% yield.

Finally, the inventors tested the possibility of preparing a few aldehydes. The inventors successfully obtained aldehydes (2r-2t) in 48-66% yield, under reaction conditions listed herein.

Spectral data and synthetic procedures for oxidation of exemplary benzylic compounds are further described hereinabove.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

What is claimed is:

1. A method of modifying a benzylic C—H bond, thereby forming a compound represented by Formula 1:

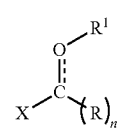

the method comprising:

irradiating a reaction mixture comprising a substrate comprising said benzylic C—H bond, oxygen and an initiator with a light, thereby forming said compound, wherein:

each X independently comprises an optionally substituted aromatic cycloalkane, an optionally substituted C3-C10 cycloalkane, or is absent;

said light is in a wavelength range sufficient for exciting the initiator, thereby generating a halogen radical;

– – – – – represents any one of: (i) a single bond if n is 2; and (ii) a double bond if n is 1;

X comprises an aromatic ring;

R is selected from the group consisting of: an alkyl, an aryl, hydrogen, and a cycloalkyl;

$R^1$ is selected from the group consisting of: hydrogen, hydroxy, or is absent;

and n is 1 or 2, wherein said initiator is represented by Formula 4:

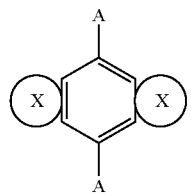

wherein each X independently comprises an optionally substituted aromatic cycloalkane, an optionally substituted C3-C10 cycloalkane, or is absent;

and each A independently represents a halo group.

2. The method of claim 1, wherein said wavelength range is from 200 to 900 nm.

3. The method of claim 1, wherein said initiator is devoid of a metal.

4. The method of claim 1, wherein said method is performed at a temperature in a range from 0 to 100° C.

5. The method of claim 1, wherein said method is performed for a time period in a range from 1 to 40 h.

6. The method of claim 1, wherein said method further comprises a preliminary step of mixing said substrate and said initiator with a solvent, thereby forming the reaction mixture.

7. The method of claim 1, wherein said substrate is at a concentration ranging from 0.01 to 2 mol/L within said reaction mixture.

8. The method of claim 1, wherein a molar ratio of said substrate to said initiator is at least 1:0.01.

9. The method of claim 1, wherein said aromatic cycloalkane is selected from the group consisting of: an aromatic ring, a fused aromatic ring and a substituted aromatic ring.

10. The method of claim 1, wherein said initiator is 9,10-dibromoanthracene.

11. The method of claim 1, wherein said substrate comprises cumene.

12. The method of claim 1, wherein said compound is cumene hydroperoxide:

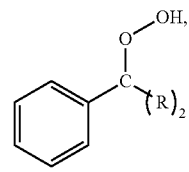

wherein R is methyl.

* * * * *